US007105351B2

(12) United States Patent
Matsubara et al.

(10) Patent No.: US 7,105,351 B2
(45) Date of Patent: *Sep. 12, 2006

(54) HANDLING METHOD OF BODY FLUID SAMPLE AND ANALYSIS APPARATUS USING THE SAME

(75) Inventors: Shigeki Matsubara, Hitachinaka (JP); Kyoko Imai, Hitachinaka (JP); Ryuji Tao, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 513 days.

This patent is subject to a terminal disclaimer.

(21) Appl. No.: 10/103,993

(22) Filed: Mar. 25, 2002

(65) Prior Publication Data

US 2002/0106803 A1 Aug. 8, 2002

(30) Foreign Application Priority Data

Jul. 27, 1998 (JP) ................................. 10-210657
Aug. 28, 1998 (JP) ................................. 10-243203

(51) Int. Cl.
G01N 35/10 (2006.01)
G01N 1/14 (2006.01)

(52) U.S. Cl. .................. 436/55; 43/47; 43/49; 43/180; 422/62; 422/63; 422/67; 422/68.1; 422/100; 422/105

(58) Field of Classification Search ............ 422/62–67, 422/68.1, 100, 105; 436/180, 43, 47, 49, 436/55
See application file for complete search history.

(56) References Cited

U.S. PATENT DOCUMENTS

| 4,683,212 A * | 7/1987 | Uffenheimer ................. 436/52 |
| 4,844,868 A * | 7/1989 | Rokugawa ................... 422/64 |
| 4,952,518 A | 8/1990 | Johnson et al. |
| 5,045,286 A * | 9/1991 | Kitajima et al. ............. 422/100 |
| 5,051,238 A | 9/1991 | Umetsu et al. |
| 5,206,568 A | 4/1993 | Björnson et al. |
| 5,218,875 A * | 6/1993 | Volpe et al. ............. 73/864.01 |
| 5,314,825 A * | 5/1994 | Weyrauch et al. ............ 436/43 |
| 5,358,691 A * | 10/1994 | Clark et al. .................... 422/64 |
| 5,470,534 A | 11/1995 | Imai et al. |
| 5,482,861 A * | 1/1996 | Clark et al. .................... 436/48 |
| 5,518,693 A * | 5/1996 | Tomasso et al. .............. 422/63 |
| 5,639,425 A | 6/1997 | Komiyama et al. |
| 5,882,863 A | 3/1999 | Imai et al. |
| 5,897,837 A | 4/1999 | Mizuno |
| 6,019,945 A * | 2/2000 | Ohishi et al. ................. 422/65 |
| 6,319,718 B1 * | 11/2001 | Matsubara et al. ........... 436/47 |
| 6,413,780 B1 * | 7/2002 | Bach et al. .................... 436/48 |
| 6,635,488 B1 * | 10/2003 | Saito et al. .................... 436/43 |
| 6,685,884 B1 * | 2/2004 | Stylli et al. ................... 422/63 |

(Continued)

FOREIGN PATENT DOCUMENTS

EP 0 148 333 7/1985

(Continued)

*Primary Examiner*—Brian R. Gordan
(74) *Attorney, Agent, or Firm*—Mattingly, Stanger, Malur & Brundidge, P.C.

(57) ABSTRACT

Sample sampling to an analysis apparatus 200 or 820 for analyzing a biochemical analysis item is performed by a pipetting device 202 or 840 which uses a repetitively used pipette nozzle, and sample sampling to an analysis apparatus 100 or 810 for analyzing an immune analysis item is performed by a pipetting device 102 or 830 which uses a disposable nozzle tip. A sample bottle containing a sample to be analyzed on both of a biochemical analysis item and an immune analysis item is sample-pipetted by the nozzle tip first, and then transported so as to be sample-pipetted by the pipette nozzle.

1 Claim, 12 Drawing Sheets

U.S. PATENT DOCUMENTS

| | | | |
|---|---|---|---|
| 6,691,748 B1 * | 2/2004 | Tajima | 141/130 |
| 6,730,517 B1 * | 5/2004 | Koster et al. | 436/47 |
| 6,835,353 B1 * | 12/2004 | Smith et al. | 422/102 |
| 6,846,457 B1 * | 1/2005 | Tokiwa et al. | 422/67 |
| 2002/0064481 A1 * | 5/2002 | Ishizawa et al. | 422/64 |
| 2002/0098117 A1 * | 7/2002 | Ammann et al. | 422/64 |
| 2002/0127727 A1 * | 9/2002 | Bach et al. | 436/48 |
| 2003/0022380 A1 * | 1/2003 | Jakubowicz et al. | 436/54 |

FOREIGN PATENT DOCUMENTS

| | | |
|---|---|---|
| EP | 02 066461 | 3/1990 |
| EP | 0 703 455 | 3/1996 |
| EP | 0 801 308 | 10/1997 |
| EP | 0 809 112 | 11/1997 |
| JP | 63200066 A * | 8/1988 |
| JP | 2-25755 | 1/1990 |
| JP | 02087069 A * | 3/1990 |
| JP | 4-169851 | 6/1992 |
| JP | 06 207943 | 7/1994 |
| JP | 9-281113 | 10/1997 |
| JP | 9-304396 | 11/1997 |

* cited by examiner

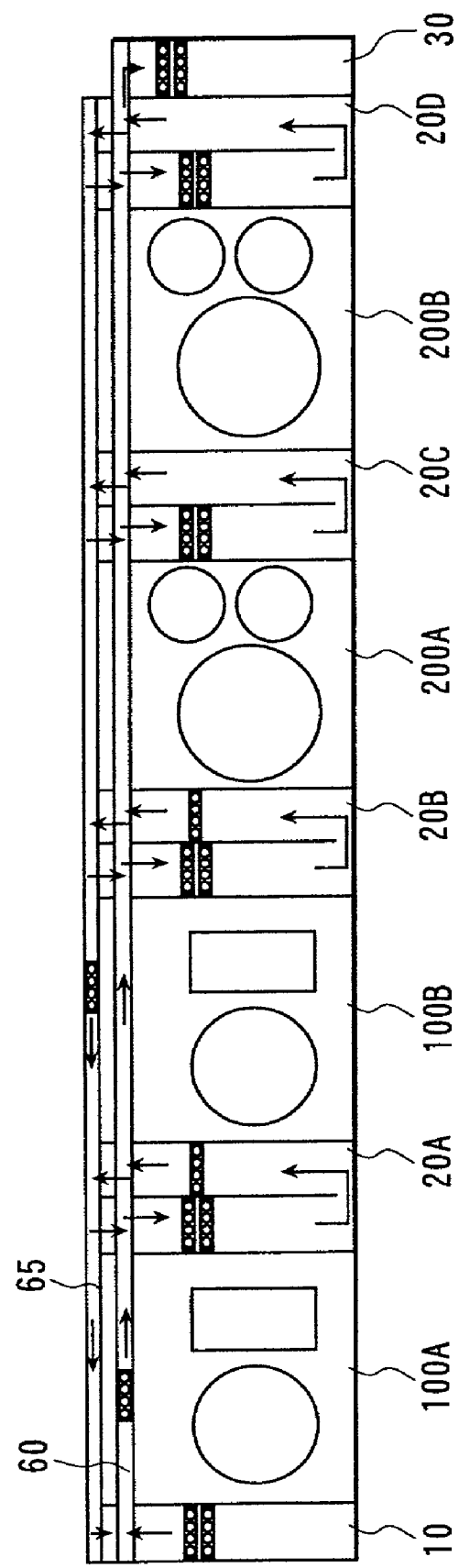

HANDLING METHOD OF BODY FLUID SAMPLE AND ANALYSIS APPARATUS USING THE SAME

BACKGROUND OF THE INVENTION

1. Field of the Invention

The present invention relates to a technology for analyzing a body fluid sample, and particularly relates to a handling method of a body fluid sample and an analysis apparatus using the handling method which can sample the body fluid samples using a plurality of pipetting devices.

2. Description of the Prior Arts

Analysis of body fluid samples such as blood and urine samples from patients is widely performed in order to diagnose pathologies, and automated analysis apparatuses are used in hospitals and clinical examination rooms.

In order to diagnose the pathologies, examination results obtainable by only one automatic analyzer are insufficient in most cases. In such a case, it is necessary to collect examination data from a plurality of analysis units. Japanese Patent Application Laid-Open Nos.9-281113 and 9-304396 disclose an analysis system which can analyze various kinds of analysis items by one system.

These prior arts propose an analysis system in which a plurality of analysis units for biochemical analysis are arranged along a sample rack transportation line, and a sample rack from a rack supply unit is dropped in at any one of the analysis units to pipette a sample on the sample rack using a pipette nozzle.

The U.S. Pat. No. 5,470,534 discloses an analysis system in which a biochemical analyzer, an immune analyzer and a nucleic acid analyzer are arranged along a transportation path for a sample bottle so that a single sample can be measured by each of the analyzers. In this prior art, whether or not the sample should proceed to a second measuring stage is determined depending on an analysis result in a first measuring stage. A biochemical analysis item is analyzed in the first measuring stage, and a sample necessary to proceed to the second measuring stage in order to identify a pathology is analyzed by the immune analyzer and/or the nucleic acid analyzer in the second stage.

On the other hand, in the apparatus automatically analyzing body fluid samples, many samples are successively pipetted usually using one pipette nozzle. Therefore, there arises a contamination problem of the following samples caused by residue of the preceding sample on the pipette nozzle. A technology in regard to carry-over of this kind is disclosed, for example, in Japanese Patent Application Laid-Open No.4-169851. In this example, analysis of a biochemical analysis item such as measurement of components usually contained in blood and analysis of an immune analysis item such as detecting an antigen or an antibody utilizing cohesive reaction of latex particles using a row of reaction containers formed in a circular shape.

Further, Japanese Patent Application Laid-Open No.4-169851 points out that useless consumption of washing solution can be prevented by spending sufficient washing time in washing a reagent pipette nozzle after pipetting a reagent for an immune analysis item using a washing solution or by increasing a delivery flow rate of the washing solution to wash the reagent pipette nozzle, and by spending short washing time in washing a reagent pipette nozzle after pipetting a reagent for a biochemical analysis item or by decreasing a delivery flow rate of the washing solution to wash the reagent pipette nozzle.

In addition, Japanese Patent Application Laid-Open No.4-169851 also points out that in a case of a sample pipette nozzle different from the reagent pipette nozzle, useless consumption of washing solution can be prevented by controlling the flow rate of the washing solution.

As an another type to pipette a body fluid sample, it is widely known to use a disposable nozzle tip. For example, U.S. Pat. No. 5,639,425 discloses a method comprising the steps of providing a tip holder at a position within a movable range of a coupling tube which can be coupled to a nozzle tip, transporting a nozzle tip from a tip rack on which many nozzle tips are arranged to the position of the tip holder, then coupling the nozzle tip with an end portion of the coupling tube on the tip holder, discharging a sample sucked inside the coupled nozzle tip into a reaction container, and after discharging the sample, removing the nozzle tip from the coupling tube at a tip detaching station.

Moreover, Japanese Patent Application Laid-Open No.2-25755 discloses an analysis apparatus in which a plurality of reaction parts are arranged near the transportation line for transporting the sample rack, and a bypass line and a sample dilution part are disposed between the transportation line and the respective reaction parts.

This reference discloses further that the plurality of reaction parts are constructed to analyze the sample by a calorimathod, an ion selective electrode method and an immunity method. In this example, the sample rack is moved from the transportation line to the bypass line by a rack changer provided in the transportation line, and a dilution arm pippetes the sample from the sample rack on the bypass line to the sample dilution part, and other pippetting arm having a different construction pippetes the sample from the sample dilution part to the reaction part. Furthermore, it is disclosed that it is preferable for the plurality of the reaction parts to be arranged in a sequence to prevent the mutual contamination between the samples.

[Discussion of the Prior Arts]

Many methods for measuring immune analysis items include an operation for binding a label substance to solid phase utilizing an antigen-antibody reaction (that is, an immune reaction).

In a case where there are needs to analyze both of an immune analysis item through such a method and a biochemical analysis item through a method of measuring an absorbance of a reaction solution produced as a result of the chemical reaction, or there are needs to analyze a DNA analysis item and biochemical analysis item, it is convenient for handling samples that plurality of analysis units are placed in an analysis system and a single sample bottle is commonly used for each of the analysis units.

However in U.S. Pat. No. 5,470,534 in connection with the analysis systems of such a type, there is no description on measures for avoiding the carry-over between samples.

Furthermore, in Japanese Patent Application Laid-Open No.9-281113 and Japanese Patent Application Laid-Open No.9-304396, plurality of analysis units are disclosed, however there is no description to arrange both of a biochemical analysis unit and a immune analysis unit, or to arrange both of the biochemical analysis unit and a DNA analysis unit.

Japanese Patent Application Laid-Open No.4-169851 proposes that the carry-over is avoided only by washing operation using a single pipette nozzle repetitively used for both of a biochemical analysis item and an immune analysis item. However, since there is a limitation in the actually applicable washing time or washing flow rate, it is difficult to eliminate the effect of carry-over on a measured value of an immune analysis item in which existence of an extremely small amount of a residual sample causes a problem.

According to the construction using the disposable nozzle tip described in U.S. Pat. No. 5,637,425, there is no problem on the effect of carry-over between samples since the nozzle tip is exchanged for each sample. However, since there are the coupling operation and the detaching operation of the nozzle tip for each sample, the method has a disadvantage in that a sufficient processing capacity can not be attained when a large volume of analysis items such as biochemical analysis items must be processed in a short time.

In a analysis apparatus described in Japanese Patent Application Laid-Open No.2-25755, there is not any difference between the construction of the plurality of the reaction parts, and it is intended to prevent the mutual contamination between the samples only by changing the arranging sequence of the reaction parts. However, the dilution arm and the pippeting arm are commonly used for all of the samples repeatedly, therefore, it becomes difficult to avoid the carry-over between the samples caused by using these arms.

SUMMARY OF THE INVENTION

[Object of the Invention]

An object of the present invention is not to be affected by carry-over between samples on a measured value of an immune analysis item though a repetitively used pipette nozzle in sample sampling for biochemical analysis items is employed.

Another object of the present invention is to provide a method and an apparatus which can prevent deterioration of the processing capacity in regard to biochemical analysis items and can avoid the carry-over between samples in regard to immune analysis items in a case where the biochemical analysis items and the immune analysis items are analyzed using separate analysis units, respectively.

A further object of the present invention is to make it possible to avoid the carry-over between samples by using both of a pipetting device of a type which samples a sample using a repetitively used pipette nozzle and a pipetting device of a type which samples a sample using a disposable nozzle.

A further object of the present invention is to provide a method and an apparatus which can process a specified sample without being affected by the carry-over between samples when being ordered to analyze both of analysis item which should highly avoid the carry-over and analysis item which does not need so much to avoid the carry-over.

A further object of the present invention is to provide an apparatus which can select a re-measurement logic and/or analysis channel for the re-measurement automatically, before the re-measurement of the sample is performed according to a measurement result of the sample once measured.

[Statement of the Invention]

The present invention is characterized by an analysis apparatus in which a sample is sampled from a single sample bottle to a plurality of receiving containers using a plurality of sample pipetting devices, and the each sample received in each of the receiving containers is analyzed, wherein the plurality of sample pipetting devices include first pipetting devices using a disposable nozzle tip and second pipetting devices using a repetitive used pipette nozzle, and operation of sampling the sample from the single sample bottle is executed by the second pipetting devices after executed by the first pipetting devices.

It is preferable that the analysis apparatus comprises at least two kinds of analysis units, and a first analysis unit has the first pipetting device using a disposable nozzle tip and a second analysis unit has the second pipetting device using a repetitively used pipette nozzle. In this case, in regard to a specified sample to be analysis measured in the first and the second analysis unit, sample sampling is executed in the first analysis unit in prior to sample sampling in the second analysis unit, and the sample sampling in the second analysis unit is executed after completing of sampling the specified sample by the first analysis unit.

The analysis apparatus comprises a standby unit for letting a sample rack which has been already executed sample sampling in the first analysis unit but not yet executed sample sampling in the second analysis unit stand by therein (the sample rack has the specified sample). The specified sample is transported to the first analysis unit from the standby unit to be sampled in the first analysis unit for re-measurement before sampling the specified sample in the second analysis unit when a measured result of the first analysis unit in regard to the specified sample is necessary to execute the remeasurement.

By constructing in such that the first analysis unit measures an immune analysis item or a DNA analysis item, and the second analysis unit measures a biochemical analysis item, the immune analysis item or the DNA analysis item is sampled before sampling relating to the biochemical analysis item.

In this case, whenever the samples are changed, the nozzle tips are changed, and the analysis measured value of the immune analysis item or the DNA analysis item is not affected by the carry-over between samples.

Furthermore, the analysis measured value of the biochemical analysis item does not receive the affection by the carry-over between samples by washing the pipette nozzle repetitively used for sampling the sample relating to the biochemical analysis item by a well-known washing method whenever the samples are changed.

In the analysis apparatus, an analysis item which needs to avoid the affection of very small carry-over between the samples, that is, a specified analysis item requiring sample sampling by a nozzle tip is pre-registered in the analysis apparatus. Such a specified analysis item is stored in a memory unit in a control unit, and if the specified analysis item is included among items to be analyzed on many samples each of which is instructed by an operator, the sample is transported initially to the first analysis unit to be sampled using a nozzle tip before it is transported the other analysis apparatus when sample sampling is performed on the sample.

A specified sample rack having a specified sample required to be analyzed in both of the first and the second analysis unit is restricted in the transportation order or the transportation path as described above, but a sample rack having only samples not required to be sampled by the nozzle tip is transported so as to be let drop in at the plurality of analysis units in arranging order depending on necessity to be sampled. In this case, the sampling process is efficiently performed.

In a case where the plurality of analysis units include a first analysis unit having a pipetting device using a disposable nozzle tip and a second and a third analysis apparatus having a pipetting device using a repetitively used pipette nozzle and the plurality of analysis units are arranged at positions in the order of the third analysis apparatus, the first analysis unit and the second analysis unit from the side near the rack supply unit, in regard to a specified sample rack having a specified sample necessary for analysis measurement in the first, the second and the third analysis apparatus, the specified sample rack being transported to the first analysis unit to execute sample sampling using the nozzle tip first, then the specified sample rack being let stand by in the standby unit, the specified sample rack on standby in the standby unit being transferred to the rack transporting apparatus through the returning line when re-measurement of the specified sample by the first analysis unit is determined to be necessary, then sample sampling for the re-measurement in the first analysis unit being executed.

Then, in the first analysis unit., the specified sample rack having the specified sample finished sampling of sample for re-measurement is transferred to the rack transporting apparatus through the returning line, and then the specified sample is sampled in the third analysis apparatus and/or the second analysis unit. On the other hand, when re-measurement of the specified sample is determined to be unnecessary, the specified sample rack on standby in the standby unit is transferred to the rack transporting apparatus through the returning line and then the specified sample is sampled in the third analysis apparatus and/or the second analysis unit.

A method of handling a body fluid sample in accordance with the present invention is characterized by that a sample rack having a sample is positioned to at least one out of a plurality of analysis units, and analysis of the sample sampled on the sample rack is performed in the analysis apparatus, wherein the method comprises the steps of processing the sample by an analyzer having a first analysis unit having a first pipetting device using a disposable nozzle tip and a second analysis unit having a second pipetting device using a repetitively used pipette nozzle; transporting a specified sample rack having a specified sample to be analyzed in the first and the second analysis unit to the first analysis unit to sample the specified sample in the first analysis unit in prior to transferring the sample rack to the second analysis unit; letting the specified sample rack finished sampling of sample in the first analysis unit temporarily stand by in a standby unit before transporting the specified sample rack to the second analysis unit; judging whether or not re-measurement of the specified sample by the first analysis unit is necessary; transporting the specified sample rack from the standby unit to the second analysis unit and sampling the specified sample by the pipette nozzle if the result of judgment is that re-measurement of the specified sample by the first analysis unit is not necessary; transporting the specified sample rack from the standby unit to the first analysis unit and sampling the specified sample for re-measurement in said first analysis unit if the result of judgment is that re-measurement of the specified sample by the first analysis unit is necessary; and transporting the specified sample rack finished sampling of the sample for re-measurement to the second analysis unit and sampling the specified sample by the pipette nozzle.

Furthermore, in the handling method of the biochemical sample based on the present invention, an image plane to for selecting the analysis items relating to the respective samples is displayed on a display device, and an indication field to indicate a necessity to avoid the carry-over between the sample relating to the selected analysis item is displayed on the display device. When the sample to be analyzed the analysis item which is indicated to need to avoid the carry-over and the analysis item which is not indicated to need to avoid the carry-over, are sampled in the analysis part, the sampling relating to the analysis item which is not indicated to need to avoid the carry-over is performed, after the sampling relating to the analysis item which is indicated to need to avoid the carry-over finishes.

In this case, the information to show the necessity to avoid the carry-over is stored in a memory device relating to the analysis item which is indicated the necessity to avoid the carry-over, after that, a memorized information may be output on the display device when the same analysis items are selected.

BRIEF DESCRIPTION OF THE DRAWINGS

FIG. 12 is an outline of a configuration of the fourth embodiment in accordance with the present invention.

DESCRIPTION OF THE PREFERRED EMBODIMENTS

In a preferred embodiment of the present invention, a sample bottle containing a body fluid sample such as blood, blood serum or urine is handled in a state of being held in a sample rack as a bottle holder. It is preferable that the sample rack can hold one or more sample bottles, but in the following embodiment, an example as that one sample rack can hold up to five sample bottles.

Figure 1:
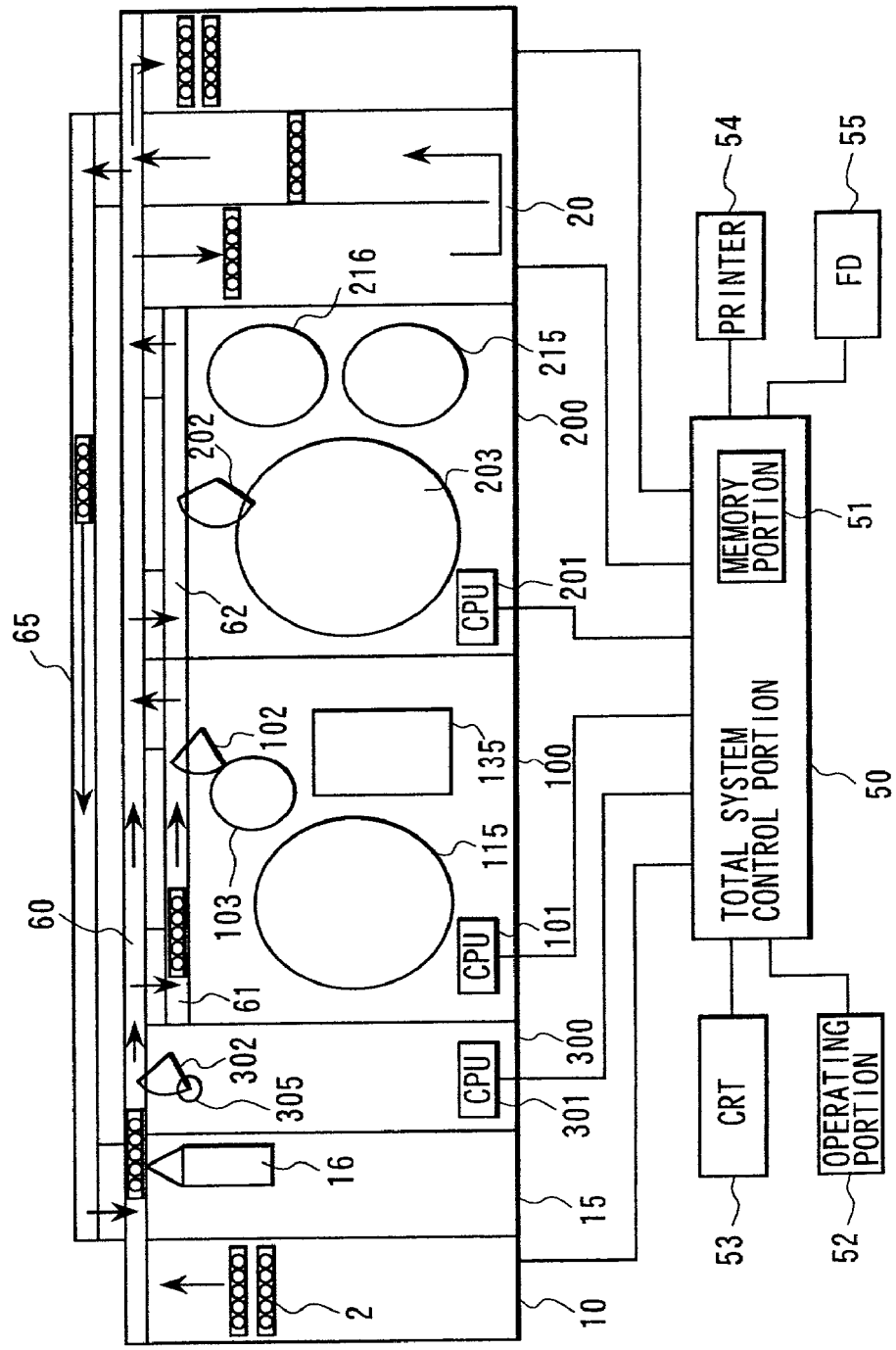
FIG. 1 is a plane view showing the outline of a configuration of an embodiment in accordance with the present invention.

FIG. 1 is a plane view showing the outline of a configuration of an embodiment of an automatic analysis apparatus to which the present invention is applied. In FIG. 1, a rack supply unit 10 is operated so as to supply a sample rack 2 to a rack transportation line 60 of a rack transportation apparatus. The rack supply unit 10 comprises an area capable of placing a tray on which a plurality of sample racks are arranged and an identification read unit 15. The rack supply unit 10 is sometimes called as a rack loading unit because the rack supply unit is loaded with the sample rack 2 having samples. The sample racks 2 supplied to the rack supply unit are pushed to an entrance side of the rack transportation line 60 one-by-one by a well-known rack pushing mechanism.

The pushed sample rack 2 is moved up to a reading position of the identification read unit 15 by a mover such as a movable hook.

The sample rack 2 is, for example, a rectangular parallelepiped shaped holder, and can hold the plurality of sample bottles 5 (Refer FIG. 2) in a row along the lateral direction of the sample rack. To the sample rack 2 of this type, a bar-code label having coded rack identification information including kind of rack and rack number is attached. In each of the sample bottle 5, a bar-code label having coded sample information such as bottle identification number, patient code, medical section number, sample receipt number is attached.

The automatic analysis apparatus of FIG. 1 comprises a rack stoker 30 orderly storing the sample racks transported by the rack transportation line 60. A electrolyte item analysis unit 300, a immune item or DNA item analysis unit 100, a biochemical analysis unit 200 and a standby unit 20 as a standby unit are arranged in this order from a position near the rack supply apparatus along the rack transportation line 60 between the rack supply apparatus 10 and the rack stoker 30.

The electrolyte item analysis unit 300 comprises a pipetting device 302 which pipettes a sample from a sample bottle on the sample rack stopping at a sample pipetting position on the rack transportation line 60 for the electrolyte item analysis unit 300 to a dilution container 305 contained in the electrolyte item analysis unit 300.

The pipetting device 302 has a repetitively used pipette nozzle, that is, a pippeting nozzle commonly used for the different samples, sucks and holds a sample in a sample container on the sample rack in the pipette nozzle, and discharges a predetermined amount of the held sample into the dilution container 305.

The sample diluted with a diluent in the dilution container 305 is conducted to a flow cell by a sucking tube (not shown), and electrolytic components contained in the sample such as sodium ion, potassium ion, chlorine ion and so on are measured using an ion selective electrode for each ion arranged in the flow cell. An analysis unit control part 301 contained in the analysis unit 300 executes calculation to obtain a concentration of each of the electrolytic components based on a detected signal of each ion, and reports the obtained measured value to a total system control unit 50.

The immune item or DNA item analysis unit 100 uses a disposable nozzle tip, as to be described later, and comprises a pipetting device 102 which is operated so as to suck a sample from a sample bottle on the sample rack positioned at a sample sampling position on a bypass line 61 into the nozzle tip, hold the sucked sample in the nozzle tip and then discharge the preset amount of the held sample into a reaction container on a reaction disk 103.

The pipetting device 102 exchanges the nozzle tip every time when the samples are changed. For example, in a case that there is one analysis item to be analyzed in the analysis unit 100 relating to a former sample, the pipetting device 102 removes the used nozzle tip after one sampling operation is performed for the former sample, and then a new nozzle tip is mounted.

On the other hand, in a case that there is three analysis items to be analyzed in the analysis unit 100 relating to the following next sample, the pipetting device 102 removes the used nozzle tip after the tree times of the sampling to the three reaction containers are performed, after that, the new nozzle tip is mounted.

When the analysis unit 100 is that used to analyze the immune analysis item, the sample pipetted in the reaction container on the reaction disk 103 is mixed with a reagent for immune reaction. After immune reaction between the sample and the reagent, an analysis item is measured through further steps if necessary. In this case, the word "immune reaction" is a synonym for antigen-antibody reaction.

When the analysis unit 100 is that used to analyze the DNA analysis item, the sample pippeted in the reaction container on the reaction disk 103, is mixed with a reagent for nucleic acid analysis, after hybridization reaction thereof, a portion combined with a label is cut out with a restriction enzyme, and analysis results of the DNA analysis items are obtained base on the measurement of the label.

A feature for obtaining a measured value of an immune analysis item utilizing an immune reaction between a sample and a reagent is a method of measuring a label substance utilizing a sold phase such as magnetic particles produced by an antibody. For example, a substance to be analyzed in a sample and a solid phase are bound by a immune reaction, and a reagent having a label substance is bound to the first complex, and then the solid phase is separated from liquid phase. The separated liquid phase is conducted to a flow cell, and the label substance is measured through fluorescence photometry or chemi-luminescence photometry. Otherwise, the solid phase after liquid separation is introduced to a photometric position, and a marker bound on the solid phase is measured through a chemi-luminescence method or an electrochemical luminescence method. An analysis unit control part 101 contained in the analysis unit 100 performs control of operation of each mechanism units in the analysis unit 100 and calculation of measured data on an analysis item.

The biochmical analysis unit 200 comprises a pipetting device 202 for pipetting a sample using a repetitively used pipette nozzle, as to be described later. The pipetting device 202 is operated so as to suck a sample from a sample bottle on the sample rack, which is positioned at a sample pipetting position on the bypass line 62 through the rack transportation line 60, into a portion near the end of the pipette nozzle, hold the sucked sample in the pipette nozzle, and then discharge the preset amount of the held sample into a reaction container on a reaction disk 203. A chemical reaction between the sample and a reagent is progressed in the reaction container, and a optical characteristic of the produced reaction solution is measured. In this example, the reaction solution is optically measured in a sate that the reaction solution is contained in the reaction container to obtain a measured value of a biochemical analysis item. An analysis unit control part 201 contained in the analysis unit 200 performs control of operation of each mechanism units in the analysis unit 200 and calculation of measured data on an analysis item.

In the analysis apparatus of FIG. 1, the rack transportation apparatus for transporting the sample rack having samples includes the rack transportation line 60, the bypass line 61 for the analysis unit 100 and the bypass line 62 for the analysis unit 200. Each of the bypass lines 61, 62 is formed nearly parallel to the rack transportation line 60, and receives the sample rack in the upstream side of the bypass line from the rack transportation line 60, and the sample rack finishing pipetting of the sample in the downstream side of the bypass line is transferred to the rack transportation line 60. The sample rack on the rack transportation line 60 and the bypass line 61, 62 is transported to a preset position by a well-known transporting means in which a belt conveyer or a movable hook is driven by a motor.

The sample rack 2 having the sample is positioned in at least one of the plurality of analysis units, and the sample is pipetted from the sample bottle on the sample rack by the corresponding analysis unit, and then the sample rack is transported to the standby unit 20. A sample rack having possibility of re-examination is let stand by in the standby unit 20 until the control unit judges necessity of re-measurement. The sample rack entering into the standby unit 20 is moved along a U-shaped path. The sample rack having no samples judged to be necessary to be re-measured from the measured results of the corresponding analysis unit is immediately contained in a rack stoker 30. However, the sample rack having any samples judged to be necessary to be re-measured from the measured results of the corresponding analysis unit is transferred from the standby unit 20 to the returning line 65, transported to the entrance side of the rack transportation line 60 from the returning line 65, transferred to the rack transportation line 60 again and transported to the analysis unit for the re-measurement to be sampled.

As described above, the standby unit 20 lets the sample rack finished sampling of sample in any one out of the plurality of analysis units temporarily stand by therein, but the sample rack finished sampling of sample in the analysis unit 100 for the immune analysis item is specially handled. That is, letting a sample instructed to be necessary for analysis and measurement by the three analysis units 100, 200, 300 or by the two analysis units 100, 200 be called as a specified sample, and letting a sample rack having the specified sample be called as a specified sample rack, the specified sample rack is initially transported to the analysis unit 100 for the immune analysis item to sample the specified sample by a disposable nozzle tip coupled with the pipetting device 102 in prior to transported to the other analysis unit. The specified sample rack is let enter into the standby unit 20 without dropping in at any other analysis unit. Then, when it is judged from a measured result of the analysis unit 100 in regard to the specified sample that execution of the re-measurement to the specified sample is necessary, the specified sample standing-by at the standby unit 20 is transferred to the rack transportation apparatus 60 through the returning line 65.

The specified sample rack to be re-measured is transported to the analysis unit 100 for the immune analysis item by the rack transportation apparatus without dropping in at any other analysis unit to be sampled the specified sample for the re-measurement. At that time, a new nozzle tip is coupled to the nozzle coupling tube of the pipetting device 102. Such operation is performed only in a case where one sample bottle is held on the sample rack. In a case of a plurality of samples, the transporting operation of the sample rack becomes complex because it is necessary to satisfy sampling of all the samples.

Operations of the rack supply unit 10, the standby unit 20, the rack stoker 30, the transportation apparatus including the transportation line 60 and the returning line 65 are controlled by the total system control unit 50. A read result by the bar code reader 16 as an identification information reading unit for the sample rack and the sample bottle is also transmitted to the total system control unit 50. The total system control unit 50 comprises a memory unit 51, and connected to an operating unit 52 with a key board, a CRT 53 as a screen display unit, a printer 54 for output an analysis result of each sample, and a floppy disk memory 55 storing an operating program of the analysis apparatus.

Since an item to be analyzed to each sample on each sample rack is pre-instructed from the operating unit 52 before starting analysis operation and stored in the memory unit 51, the total system control unit 50 compares read information by the bar code reader 16 with the stored analysis item information and can be determine an analysis unit to which each sample rack should be transported based on the comparison result.

In the example of FIG. 1, one set of the analysis unit 100 used for analysis measurement of an immune analysis item and one set of the analysis unit 200 used for analysis measurement of a biochemical analysis item are arranged. Two or more sets of these analysis unit for each may be arranged along the rack transportation line 60.

Figure 2:
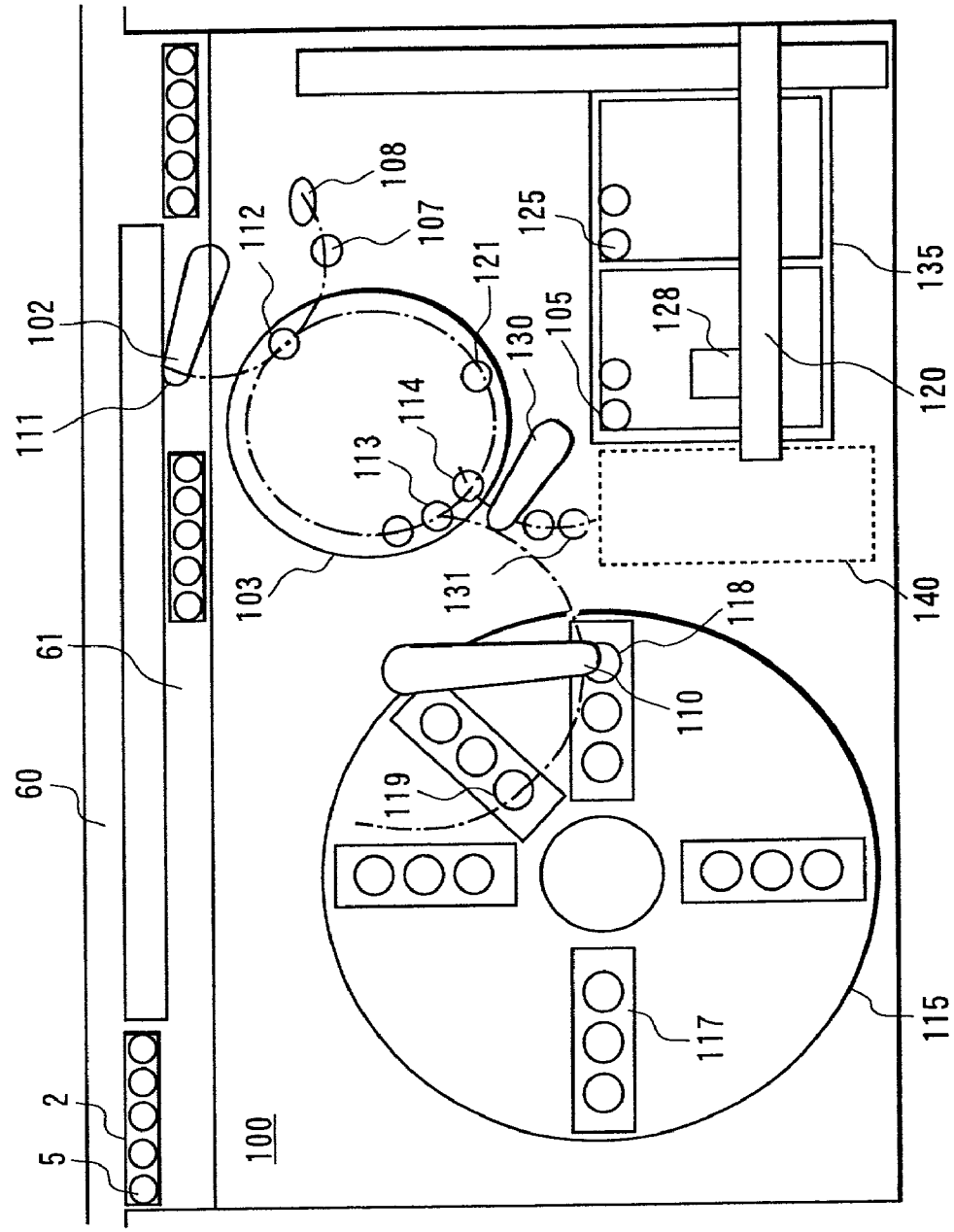
FIG. 2 is an enlarged plane view showing an analysis unit for the immune analysis items of the analysis apparatus shown in FIG. 1.

An example of the construction of the unit for the immune analysis item will be described in detail below, referring to FIG. 2 and FIG. 3. The first analysis unit 100 comprises the pipetting device 102 for pipetting a sample, a reaction disk 103 having a constant temperature maintaining function and capable of rotationally moving the mounted reaction containers 105, a rotatable reagent disk 115 on which reagent bottles 117 are arranged along the circumference combining a plural kinds of reagents for each analysis item, a reagent pipetter 110 for pipetting a reagent from the reagent bottle 117 to the reaction container 105 on the reaction disk 103, a sipper mechanism 130 for introducing a mixed solution of the sample and the reagent formed on the reaction disk 103, an unused reaction container 105 placed in a part supply area 135 and a carriage mechanism 120 for transporting an unused nozzle tip 125 to a predetermined position by a gripper.

Figure 3:
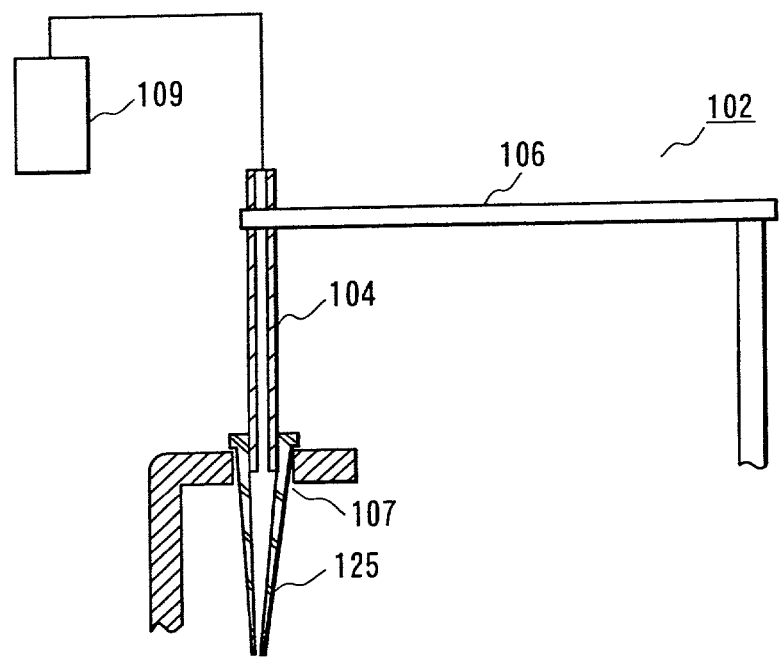
FIG. 3 is a view for explaining operation of a pipetting device in the analysis unit shown in FIG. 2.

The pipetting device 102 for sampling a sample has a coupling tube 104 capable of detachably coupling with the disposable nozzle tip 125 shown in FIG. 3. The coupling tube 104 is connected to a pump system 109 having a sucking and discharging mechanism, and supported to a movable arm 106 movable in the vertical direction and rotatable in the horizontal direction.

When analysis operation is started, the transportation mechanism 120 grips a disposable unused reaction container 105 placed in the part supply area 135 by the gripper 128 to transport it to the reaction disk 103, and releases gripping at a position 121 to put the reaction container on the reaction disk. Then, the transportation mechanism 120 grips the unused nozzle tip 125 placed in the part supply area 135 by the gripper 128 and releases gripping at a coupling position 107 to put the nozzle tip on the coupling position.

The sample rack 2 transported from the rack supply unit 10 through rack transportation line 60 is transferred to the bypass line 61 of the analysis unit 100, and moved to a sample sampling position 111. The pipetting device 102 positions the movable arm 106 to the coupling position 107, and moves down the coupling tube 104 to engage the unused nozzle tip 125 with the end of the coupling tube 104 (refer to FIG. 3). Then, the pipetting device 102 rotates the coupling tube 104 to the sampling position, and inserts the end of the nozzle tip 125 up to slightly lower than the liquid surface of the sample in the sample bottle 5 on the sample rack to suck a preset amount of the sample in the nozzle tip 125 and hold it there.

Since the unused reaction container 102 has been moved from the position 121 to a discharging position 112, the pipetting device 102 discharges the preset amount of the sample held in the nozzle tip 125 to the reaction container 105 placed at the discharging position 112. After the sampling is repeated necessary times relating to the one sample, the pipetting device 102 moves the coupling tube 104 to a detaching position 108 to remove the used nozzle tip 125 from the coupling tube 104. The removing operation of the nozzle tip is performed by bringing the upper end surface of the nozzle tip in contact with a lower surface of a split groove larger than an outer diameter of the coupling tube 104 and smaller than an outer diameter of the upper end of the nozzle tip 125, and then moving the coupling tube 104 upward. The removed nozzle tip is collected in a disposal box. In a case where there are a plurality of analysis items to be analyzed by the analysis unit 100 on a sample in a single sample bottle, one nozzle tip is continuously used for sampling the samples of these analysis items. After that, the nozzle tip is removed from the coupling tube 104. By doing so, number of consumed nozzle tips can be reduced.

The reaction container receiving the sample is moved to a reagent receiving position 113 by the reaction disk 103. The reagent pipetter 110 sucks a dispersed solution of fine magnetic particles as a solid phase into the pipette nozzle at a position 118, and discharges the dispersed solution to the reaction container on the reagent receiving position 113. Thus, a first immune reaction of binding a substance to be analyzed in the sample, for example, an antigen to the solid phase is started. After a predetermined time, a reagent containing a label substance sucked into the pipette nozzle is discharged from the reagent pipetter 110 at the position 119 into the reaction container again positioned at the reagent receiving position 113. Thus, a second immune reaction of binding the label substance to the substance to be analyzed in the reaction container is started. The pipette nozzle of the reagent pipetter 110 is used by washing every reagent pipetting.

After that, the reaction container 105 containing the reaction solution of the immune reaction is positioned at a sucking position 114 by the reaction disk 103. The sipper mechanism 130 introduces the reaction solution to a detection unit 140 from the reaction container at the sucking position 114 through a sucking nozzle. In the detection unit 140, the liquid phase containing substance not binding with the magnetic particles flows through while the magnetic particles are being attached onto the wall surface by a magnet. By doing so, the solid is separated from the liquid phase. The separated liquid phase is conducted to a measuring unit to measure fluorescence or chemi-luminescence of the label substance contained in the liquid phase. Otherwise, the separating position and the measuring unit are commonly used, and measurement is performed by generating chemi-luminescence or electro-chemical-luminescence from the label substance binding with the magnetic particles through the substance to be analyzed. After that, the sipper mechanism 130 sucks a washing solution from a washing tank 131 through the sucking nozzle to wash the flow passage of the detection unit 140. The used reaction container is removed from the reaction disk 103 by the transportation mechanism at the position 121.

An example of the construction of the analysis unit for the biochemical analysis item in FIG. 1 will be described below in detail, referring to FIG. 4. The analysis unit 200 for analyzing a biochemical analysis item comprises a reaction disk 203 on which transparent reaction containers 205 are concentrically arranged. Water maintained at a preset temperature (for example, 37° C.) is supplied to a constant temperature bath of the reaction disk 203 from a constant temperature water supply unit 230. There are two sets of reagent supply systems, and a reagent selected out of many reagent bottles 217 arranged in the first reagent disk 215 is pipetted to the reaction container 205 on the reaction disk 203 by a reagent pipetter 210, and a reagent selected out of many reagent bottles 218 arranged in the second reagent disk 216 is pipetted to the reaction container 205 on the reaction disk by a reagent pipetter 211. A mixer 219 mixes a mixture of the sample and the reagent in the reaction container.

The pipette unit 202 for pipetting a sample comprises a pipette nozzle 225 capable of sucking and discharging liquid, and can position the pipette nozzle at a sample pipetting position on the bypass line 62, a sample discharging position 204 on the reaction disk 203 and a probe washing tank 207. The pipette nozzle 225 finishing pipetting a sample on the sample rack 2 is washed in an outer wall surface and an inner wall surface of the pipette nozzle with a washing solution in the probe washing tank 207 before pipetting another sample, and repetitively used for many samples.

A reaction solution between the sample and the reagent formed in the reaction container 205 on the reaction disk 203 is irradiated with a light beam from a multi-wavelength light source 235 in a state of contained in the reaction container. The light passed through the reaction container is converted to a spectrum by a multi-wavelength photometer 240 to selectively detect a wavelength corresponding to an analysis item, and the measured light signal is digitized by an analogue-digital converter 245 and input to an analysis unit control part 201 to be calculation processed. The reaction container finishing photometrical measuring is washed in a container washing unit (not shown) and moved to the sample discharging position so as to receive a new sample.

Figure 4:
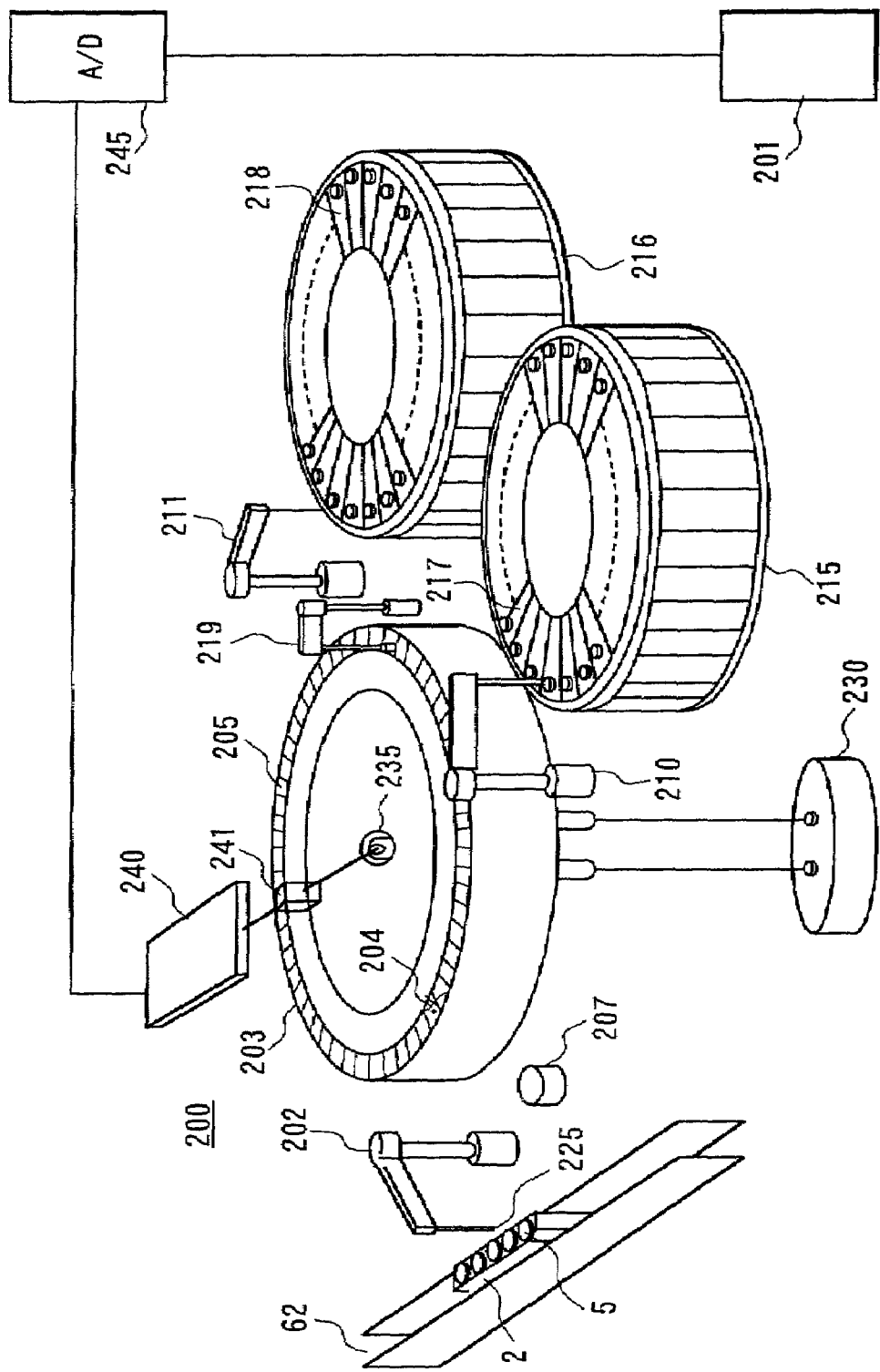
FIG. 4 is an enlarged perspective view showing an analysis unit for the biochemical analysis items of the analysis apparatus shown in FIG. 1.

In the analysis unit 200 of FIG. 4, the sample rack 2 transferred to the bypass line 62 through the rack transportation line 60 is positioned at the sample sampling position on the bypass line 62. The pipetting device 202 inserts the end of the pipette nozzle 225 up to slightly lower than the liquid surface of the sample in the sample bottle 5 at the sample pipetting position and sucks a preset amount of the sample in to a portion near the end of the probe and hold it there, and then moves the pipette nozzle 225 to the sample discharging position 204 of the row of the reaction containers. After that, the sample held in the probe is discharged into a washed reactor container placed at the discharge position 204.

The reaction container 205 receiving the sample is moved to a first reagent adding position by the reaction disk 203, and the first reagent corresponding to the analysis item is pipetted into the reaction container by the reagent pipetter 210. Then, the mixture in the reaction container is mixed by the mixing mechanism 219 to progress the chemical reaction between the sample and the reagent. In a case of an analysis item requiring a second reagent, the second reagent is further added to the reaction container at a second reagent adding position by the reagent pipetter 211. The reaction container containing the reaction solution is moved so as to cross a light beam of a photometrical position 241, and an absorbance of the reaction solution is measured based on the transmitting light at that time, and a concentration of the substance to be measured or an enzyme active value in the sample is calculated by the analysis unit control part 201 and the measured result is stored in the memory unit 51 of the total system control unit 50.

An example of operation of the automatic analysis apparatus in the embodiment of FIG. 1 will be described below, referring to FIG. 5 to FIG. 7. Before starting analysis operation, analysis items required for each sample from a patient are input through the operating unit 52. Each of the sample is usually requested to perform analytical examination on a plurality of analysis items. In the automatic analysis apparatus, an analysis item having a high necessity to avoid the carry-over is preset and stored in the memory unit 51 of the total system control unit 50.

When setting of analysis condition is instructed from the operating unit 52, an analysis condition setting screen 70 is displayed on the CRT 53 as a screen display unit. This screen 70 comprises a button 71 for invoking a routine operation screen, a button 72 for invoking a reagent control screen, a button 73 for invoking a calibration screen, a button 74 for invoking an quality control screen, and a button 75 for invoking a utility screen arranged in an upper section, as shown in FIG. 5. By touching each of the buttons with a finger by a touching panel method, or by clicking each of the buttons with a pointer by operating a mouse, the corresponding screen is displayed in the central portion. FIG. 5 shows an example of invoking a corresponding screen by touching the utility screen invoking button 75. A help button 76 is arranged below the analysis condition setting screen 70, and by touching this button 76 an explanation sentence for screen operation is displayed.

A button 81 for instructing stopping the analysis apparatus, a button 82 for instructing stopping sampling operation during analysis operation, a button 83 for invoking an alarm screen, a button 84 for invoking a screen showing states of each analysis unit and rack transportation, a button 85 for instructing printing to the printer 54, a button 86 for instructing starting the analysis apparatus are arranged in an area in the right hand side or the left hand side of the analysis condition setting screen 70. Each of the above-mentioned buttons is always displayed when the analysis condition setting screen 70 is displayed.

Here, when the utility screen invoking button 75 is selected, screen invoking buttons for system 151, maintenance 152, application 153, calculation item 154, carry-over 155, report 156 and unit configuration 157 appear in a display area 150, and a button 161 for instructing adding, a button 162 for instructing writing of data base to a floppy disk memory, a button 163 for instructing deleting and a button 164 for instructing reading from the floppy disk memory appear. When the button 153 for invoking an application screen is selected in this state, a table of list 170 showing a plurality of analysis items and sample kinds appears, and detailed screen invoking buttons 171 to 174 appear.

Figure 5:
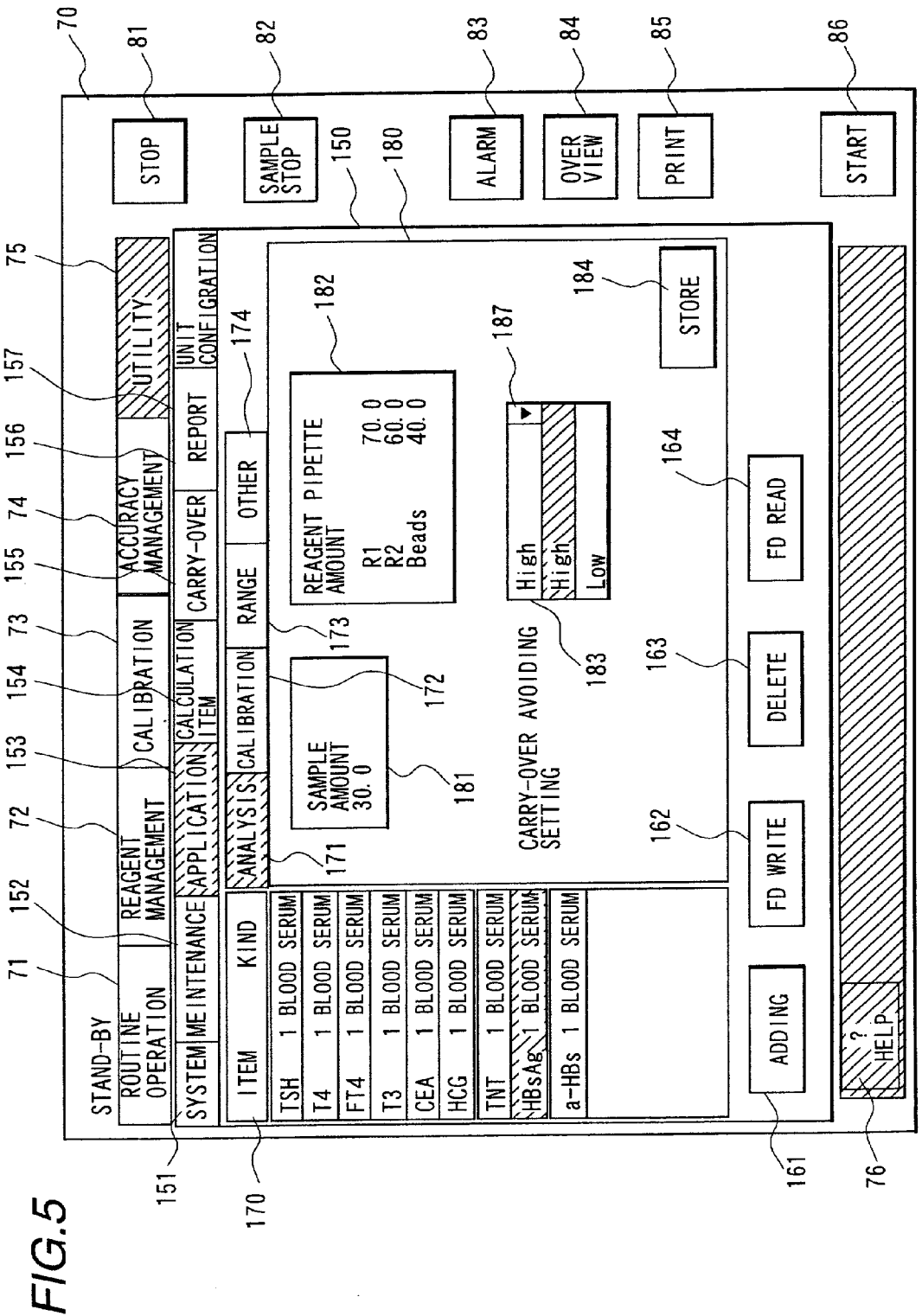
FIG. 5 is a view for explaining a screen for setting a sample volume, a reagent volume and a carry-over avoiding level.

When the analysis button 171 out of the detailed screen invoking buttons is further selected, a screen shown in FIG. 5 appears in a display area 180. That is, a section 181 for setting an amount of sample, a section 182 for setting an amount of pipetted reagent, a level setting section 183 for setting a carry-over avoiding level and a button 184 for instructing storing are displayed.

In the analysis items displayed in the table of list 170 in the screen of FIG. 5, TSH means thyrotropin, T4 means thyroxine, TF4 means free thyroxine, CEA means carcinoembryonic antigen, HCG means human chorionic gonadotropin, TNT means troponin T, HBSAg means hepatitis B surface antigen, and a-HBs means hepatitis B surface antibody. All of these are immune analysis items.

Here, it is assumed that HBsAg out of the analysis items in the table of list 170 is selected, and 30 µl of sampling amount of sample is input to the sample amount setting section 181, and 70 µl of adding amount of the first reagent R1, 60 µl of adding amount of the second reagent R2 and 40 µl of adding amount of beads reagent are input to the reagent pipette amount setting section 182. It is also assumed that in the carry-over avoiding level setting section 183, a level "High" is selected between "High" and "Low". The level selection of high and low can be performed using a level selection button 187. Then, when the storing instruction button 184 is selected, the sample amount and the reagent pipetting amounts in regard to the analysis item of HBsAg and the avoiding level of carry-over between samples corresponding to the analysis item are instructed, and stored in the memory unit 51.

Then, by selecting another analysis item displayed in the table of list 170 and similarly setting a sample volume, a reagent pipetting volume and a carry-over avoiding level corresponding to the item, these conditions can be successively set. On the other hand, by constructing so that a plurality of analysis items are selected and a common carry-over avoiding level may be instructed, the carry-over avoiding level can be instructed to the plurality of analysis items at once.

The level "High" in the carry-over avoiding level setting section 183 is for performing sample sampling under a condition of no carry-over between samples and, in more detail, the total system control unit 50 controls a transporting destination of a corresponding sample rack so as to perform sampling of the sample by a pipetting device using the disposable nozzle tip to be exchanged by a new one for each sample. In a case where the "High" level is instructed on a specified analysis item, the memory unit 51 stores the specified analysis item requiring pipetting using a disposable nozzle tip. On the other hand, the level "Low" is an instruction that sampling of the sample may be performed by a pipetting device having the pipette nozzle repetitively used for many samples by washing it, and an analysis item corresponding to this case can be analyzed in the analysis unit 200 and/or the analysis unit 300 in FIG. 1.

The analysis condition set through the setting screen as shown in FIG. 5 is continuously used corresponding to each analysis item unless the condition is changed after that. Therefore, when an examination of a patient sample is requested, the analysis condition set in FIG. 5 is automatically applied if an analysis item to be described later is input.

In this way, in the analysis apparatus shown in FIG. 1, a special method to avoid the carry-over between the samples, is needed, that is, when the analysis item is indicated as being in a level of "high", an indicated information thereof as being in a level of "high" is stored in a memory device. After that, when the same analysis item with that which is already indicated in order to set a new analysis condition, is selected by referring the analysis condition setting screen 70, the stored information, that is, the information having a necessity to avoid the carry-over operates so as to be output on the display device. In the case shown by FIG. 5, when the analysis item is selected, information "high" is displayed on the level setting section.

An operator work at starting routine analysis work will be described below. By selecting the button 71 for invoking a routine operating screen in the analysis condition setting screen 70, an item selecting screen as shown in FIG. 6 is displayed in the large display area 150 on the CRT 53. A section 251 for selecting a sample kind, a section 252 for inputting a sample number, a section 253 for inputting a patient identification number, a section 254 for selecting a kind of sample cup, an area 255 for selecting an analysis item, a button 256 for instructing a preceding sample, a button 257 for instructing a following sample and a button 258 for instructing registering are displayed in this screen. The analysis item selecting area 255 among these has a reservation registering function of 5-page capacity, and each of the pages has 24 item inputting sections or analysis item selecting sections. When the preceding sample instructing button 256 is selected, analysis item information on a sample preceding a sample displayed at present by one is displayed instead of the contents displayed at present. When the following sample instructing button 257 is selected, analysis item information on a sample following a sample displayed at present by one is displayed.

Figure 6:
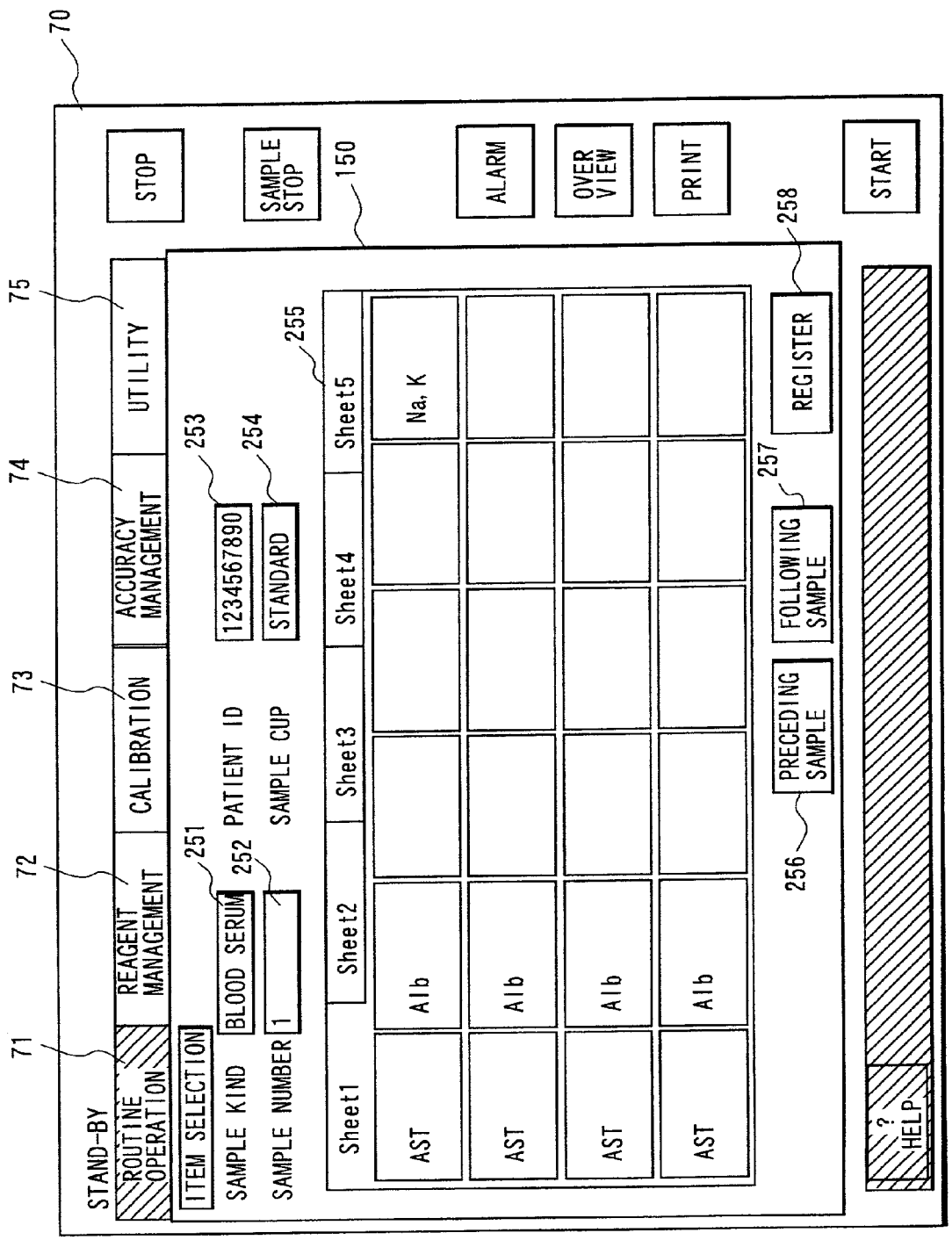
FIG. 6 is a view for showing an example of a screen for selecting a designated analysis item for each sample.

Therein, the screen of FIG. 6 shows analysis items selected by the first page of the analysis item selecting area 255. In the displayed analysis items, AST means asparatate aminotransferase, ATL means alanine aminotransferase, IP means inorganic phosphorus, TP means total protein, Alb means albmin, LD means lactate dehydrogenase, UA means uric acid, CRE means creatinine, Na means sodium ion, and K means potassium ion.

FIG. 6 is an example of selecting 10 items of biochemical analysis items to be analyzed in the first page in regard to a blood serum sample of sample number 1. FIG. 7 is an example of selecting 7 items of immune analysis items to be analyzed in the second page in regard to the blood serum sample of the same sample number. By selecting the registration instructing button 258 after finishing inputting all the analysis items requested to examine on the single sample, analysis measurement of the plurality of analysis items on the sample is reserved and stored in the memory unit 51. Since the screen of the display area 150 is updated by this registering operation, analysis item selection on a sample of the next sample number can be performed. Thus, the operator can successively perform analysis item selecting work on all the requested samples. In the example of FIG. 6 and FIG. 7, 17 analysis items on the sample of sample number 1 are registered as a result.

By selecting the reagent control screen invoking button 72 of the analysis condition setting screen, the screen for setting analysis items to be analyzed and measured to each of the analysis units in the analysis apparatus of FIG. 1 is displayed. Such allocation of analysis items to each of the analysis units is performed in prior to the inputting work of requested analysis items for each sample as shown in FIG. 6. When a process of which analysis item is allocated to which analysis units, the carry-over avoiding level between samples set in FIG. 5 is reflected. That is, an analysis item of "High" level is allocated to the analysis unit 100 having the pipetting device using the disposable nozzle tip.

On the other hand, when items to be analyzed are instructed for each sample in routine work, the relationship between analysis item and carry-over avoiding level and the analysis items allocated to each analysis unit are already registered in the control unit of the automatic analysis apparatus. Therefore the control unit checks a requested analysis item, for example, on a sample of sample number 1, and judges which analysis unit among the plurality of analysis units the sample is analyzed in. For example, since the sample of sample number 1 is relates to the analysis unit 300 in its electrolytic component, to the analysis unit 100 in its immune analysis item and to the analysis unit 200 in its biochemical analysis item, in the example of the construction of FIG. 1 the sample is analyzed in all the analysis units.

Figure 7:
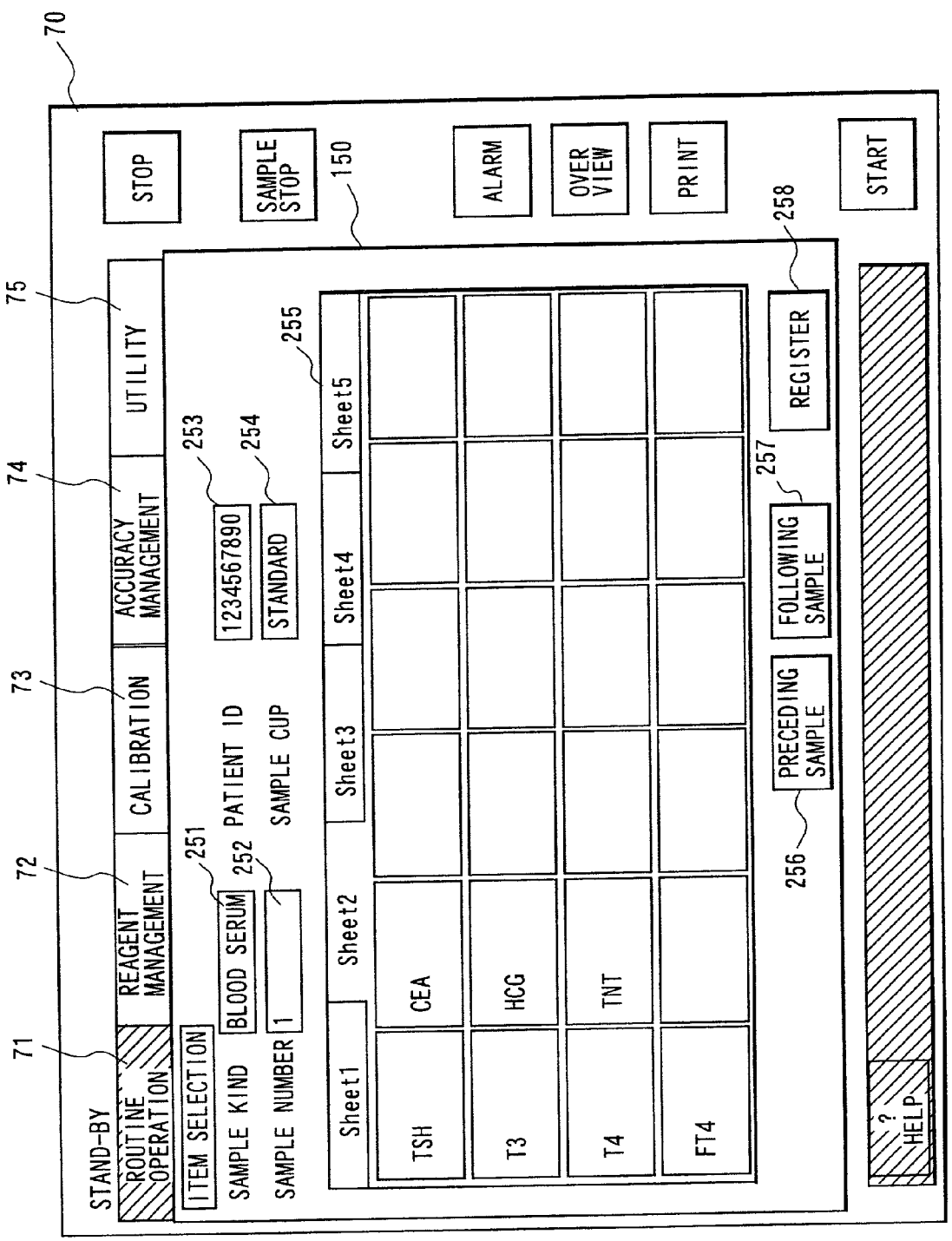
FIG. 7 is a view showing an example of the screen for selecting a designated analysis item for the same sample as that in FIG. 6.

In the cases that the analysis conditions for the respective analysis items are set by using the screens shown in FIGS. 5 to 7, the screen which is used to select the analysis item to be set the analysis condition, is displayed on the display device, and the indication field to be able to indicate the necessity to avoid affection of the carry-over between the samples corresponding to the analysis item selected on the screen, is displayed on the display device.

After that, when the samples to be analyzed the analysis items which is indicated the necessity to avoid the carry-over and which is not indicated the necessity to avoid the carry-over through the display device, are sampled in the analysis part such as the analysis units 100, 200, 300 etc., the sampling of the sample relating to the analysis item not indicated the necessity is executed after the sampling of the sample relating to the analysis item indicated the necessity is executed.

An example of handling a sample in the automatic analysis apparatus of FIG. 1 will be described below. For the purpose of convenience, it is assumed that a single sample analyzed on an electrolytic substance analysis item and a biochemical analysis item is held on the first sample rack firstly supplied from the rack supply unit 10 to the rack transportation line 60, and a single sample analyzed on an electrolytic substance analysis item, a an immune analysis item and a biochemical analysis item is held on the second sample rack secondarily supplied. In a case where a plurality of samples are held on a single sample rack, the transportation rout of the sample rack is determined so that sample sampling of analysis items relating to all the samples is performed.

The first sample rack pushed out from the rack supply unit 10 to the transportation apparatus side is positioned at the reading position of the identification reading unit 15, and the bar code label of sample information attached to the sample bottle is read by the bar code reader 16. The total system control unit 50 determines analysis unit at which the first sample rack should drop in by comparing the read information with analysis information instructed to the samples, and recognizing based on the compared result that there is no specified analysis item requiring sampling by the nozzle tip, and recognizing requested analysis items corresponding to analysis items allocated to each of the analysis units.

Since the first sample rack has no samples requiring analysis by the analysis unit 100 for the immune analysis item, the total system control unit determines that the first sample rack is transported so as to drop in at the analysis unit 300 for the electrolytic analysis item placed in the position near the rack supply unit 10, and then drop in at the analysis unit 200 for the biochemical analysis item. That is, the sample racks in this case, are transported to the plurality of the analysis units according to the arranging order thereof and depending on the necessity. Both of the second analysis unit 200 and the third analysis unit 300 are analysis units having the pipetting device using the repetitively used pipette nozzle.

The first sample rack of which the identification information has been read is moved to the sample sampling position of the analysis unit 300 for the electrolytic analysis item, and the pipetting device 302 sucks a part of the sample on the sample rack and discharge it to the diluting container 305 as a receiving container. The first sample rack finishing sample sampling at the analysis apparatus 300 is transported to the analysis unit 200 for the biochemical analysis item without dropping in at the analysis unit for the immune analysis item.

The first sample rack is once stopped at the entrance of the bypass line 62 and then transferred to the bypass line 62, and positioned at the sample sampling position on the bypass line 62. The pipetting device 202 repeats operation of pipetting the sample in the sample bottle on the first sample rack to a plurality of reaction containers 205 number of which is corresponds to number of items to be analyzed. After finishing sample sampling for a predetermined number of analysis items, the first sample rack is transferred to the rack transportation line 60, and then transported to the standby unit 20.

If the control unit judges that the analysis result by each of the analysis apparatus does not require any re-measurement, the first sample rack goes out of the standby unit 20 and is stored in the rack stoker 30. If the control unit judges that the analysis results by the analysis unit requires re-measurement on one or more analysis items, the first sample rack on standby in the standby unit 20 is transferred to the returning line 65 to transported to the entrance side of the rack transportation line 60, and then transported to the analysis unit 200 again by the transportation line 60. After plural times of sample sampling corresponding to number of analysis items for re-measurement, the first sample rack is stored in the rack stoker 30 through the transportation line 60. The analysis results in regard to the sample on the first sample rack by the units 200, 300 may be output to the CRT 53 and the printer 54.

While the first sample rack is under processing, the second sample rack may be supplied from the rack supply unit 10 to the entrance side of the rack transportation apparatus. The second sample rack is moved to the reading position of the identification reading unit 15, and the sample information expressed by the bar code on the outer wall of the sample bottle is read by the bar code reader 16. The control unit determines analysis unit at which the second sample rack should drop in by checking the analysis condition set information and the instructed information input or selected by the operating unit 52 and the read information in regard to the sample on the second sample rack. Since the body liquid sample held on the second sample rack is instructed so as to be analyzed on an electrolytic analysis item, an immune analysis item and a biochemical analysis item, it is determined that the second sample rack drops in the analysis units 100, 200 and 300 in the construction example of FIG. 1.

In this case, the control unit recognizes that the specified analysis item requiring pipetting by the disposable nozzle tip is included among the plurality of analysis items instructed to perform analysis, and determines that the second sample rack is transported firstly to the analysis unit 100 which can perform such pipetting. Based on the determination, the control unit controls operation of the rack transportation apparatus so that the second rack is transported to the analysis unit 100 in prior to transporting to the other analysis units. An analysis item allocated to the first analysis unit is not limited to an immune analysis item, but an analysis item set to "High" in the carry-over avoiding level between samples as shown in FIG. 5 may be allocated to the analysis unit 100 even if it is a biochemical analysis item.

Based on the above-mentioned determination of the transportation order, the second sample rack in the identification reading unit 15 is transported to the bypass line 61 corresponding to the analysis unit 100 arranged in the second order through the rack transportation line 60 without dropping in at the analysis unit 300 which is the closest to the rack supply unit, and positioned at the sample sampling position on the bypass line 61. The pipetting device 102 couples the unused disposable nozzle tip 125 with the coupling tube 104, and repeats operation of pipetting the sample in the sample bottle on the second sample rack to a plurality of reaction containers 105 number of which is corresponds to number of items to be analyzed. The second sample rack after finishing sampling is transferred from the bypass line 61 to the rack transportation line 60, and then transported to the standby unit 20 without dropping the analysis unit 200 arranged in the third order.

While the second sample rack is temporally standing by at the standby unit 20, analysis measured results of the sample by the analysis unit 100 can be obtained. Based on the analysis measured results by the analysis unit 100, the control unit judges necessity of re-measurement on each of the measured analysis items is necessary. If the judged result is that re-measurement is unnecessary to any analysis items, the second sample rack on standby in the standby unit 20 is transferred to the returning line 65, and transported to the entrance side of the rack transportation line 60 by the returning line 65. Then, the second sample rack drops in at the analysis unit 300 for the electrolytic analysis item, and the pipetting device 302 pipettes the specified sample using the pipette nozzle. After that, the second sample rack is transported to the analysis unit 200 arranged in the third order without dropping in at the analysis unit 100, and positioned at the sample sampling position on the bypass line 62, and the pipetting device 202 pipettes the specified sample using the pipette nozzle 225.

The second sample rack finishing pipetting in the analysis unit 300 and the analysis unit 200 is transported to the standby unit 20 to temporally stand by at there. Then, necessity of re-measurement is judged based on the analysis measured results by the analysis units 200 and/or the analysis units 300. If re-measurement is unnecessary, the second sample rack is stored in the rack stoker 30. If re-measurement is necessary, the second sample rack is transported to the third analysis unit 300 and/or the second analysis unit 200 again to be sampled for the re-measurement. After that, the second sample rack is transported to and stored in the rack stoker 30.

On the other hand, when based on the analysis measured result by the analysis unit 100 for the immune analysis item, it is judged that re-measurement on any of the analysis items is necessary, the control unit transports the second sample rack as follows. That is, The second sample rack holding a specified sample is transferred from the standby unit 20 to the returning line 65, and transported to the entrance side of the rack transportation line 60 by the returning line 65, and then transferred to the rack transportation line. The rack transportation line 60 transports the second sample rack to the bypass line 61 corresponding to the analysis unit 100 without dropping in at the analysis unit 300. At this time point, sample sampling of the second sample rack is not performed by the other analysis units 200 and 300 yet.

The pipetting device 102 of the analysis unit 100 pipettes the specified sample on the second sample rack positioned at the sample sampling position on the bypass line to the reaction container 105 on the reaction disk 103 using a new disposable nozzle tip in order to measure the analysis item which is judged that re-measurement is necessary.

The second sample rack finishing sample sampling for re-measurement is once transferred to the rack transportation line 60, and immediately transported to bypass line 62 corresponding to the analysis unit 200. Then, the first sample sampling of the second sample rack by the pipette nozzle 225 of the pipetting device 202 is performed. The second sample rack finishing sample sampling in regard to the specified sample is transferred to the returning line 65 through the rack transportation line 60, and then transferred to the rack transportation line 60 to be transported to the third analysis unit 300. After that, the first sample sampling in regard to the specified sample by the pipette nozzle of the pipetting device 302 is performed.

Otherwise, it is possible to control so that when sample sampling for re-measurement in regard to the analysis unit 100 is finished, the second sample rack is transferred to the rack transportation line 60, successively transferred to the returning line 65, transported from the entrance side of the rack transportation line 60, and sample sampling is performed in the analysis unit 300 and then in the analysis unit 200 in regard to the specified samples, respectively. In any case, the second sample rack finishing sample sampling in the analysis units 200 and 300 is transported to the standby unit 20 to temporally stand by at there until the judgment on necessity of the re-measurement is output. The transporting operation in regard to the second sample rack after judgment on necessity of the re-measurement is the same as that described above.

Depending on a patient sample, there is a case where analysis by only one analysis unit out of the three analysis units shown in FIG. 1, analyses by the two analysis units for the immune analysis item and the biochemical analysis item, or analysis by the two analysis units for the immune analysis item and the electrolyte analysis item is performed. In a case where a sample is analyzed by the analysis unit 100 and the analysis unit 200 or 300, the system is constructed so that the sample is initially sampled in the analysis unit 100, then the sample sampling for re-measurement is performed in the analysis unit 100, and then sampling operation of the sample in the same sample bottle is performed in the other analysis unit 200 or 300.

As described above, in the embodiment of the apparatus of FIG. 1, since sample sampling is performed in the analysis unit having the pipetting device using the disposable nozzle tip and then sample sampling is performed in the analysis unit having the pipetting device using the repetitively used pipette nozzle by washing, an analysis item which must strictly avoid an effect of carry-over between samples can be analyzed with keeping high reliability. Further, since an analysis item which is not so strongly affected by an effect of carry-over between samples is sampled by the pipetting device using the repetitively used pipette nozzle, the total processing capacity of the analysis apparatus is not reduced so much. Because number of analysis items using the pipette nozzle is much larger than number of items necessary to use the disposable nozzle tip.

Another embodiment of the construction of an analysis apparatus in accordance with the present invention will be described below, referring to FIG. 8. The automatic analysis apparatus for analyzing body fluid samples of FIG. 8 comprises a sample bottle transportation apparatus 800, a first analysis unit 810 for analyzing the immune analysis item and a second analysis unit 820 for analyzing the biochemical analysis item. The sample bottle transportation apparatus 800 has a rotatable sample disk 801 capable of holding many sample bottles 802 in circular shape.

A first pipetting device 830 is a pipetting device using a disposable nozzle tip by exchanging it for each sample. A second pipetting device 840 is a pipetting device using a repetitively used pipette nozzle by washing. The first analysis unit 810 has a reaction container exchange apparatus 813 for exchanging a used reaction container with a unused reaction container and capable of exchangeably arranging many reaction containers 812 on a reaction disk 811. A necessary reagent corresponding to an immune analysis item is pipetted from a reagent supply unit 816 into the reaction container 812 on the reaction disk 811.

The first pipetting device 830 can couples the unused disposable nozzle tip to a tip coupling tube on a tip supplier 814. The used nozzle tip is removed from the coupling tube to be disposed to a disposal box 815. The first analysis unit 810 has a measuring unit 815 for measuring a reaction solution or a solid phase after immune reaction. A reaction disk 821 in the second analysis unit 820 has a row of transparent reaction containers 822. A necessary reagent corresponding to a biochemical analysis item is pipetted from a reagent supplier 826 to these reaction containers 822. The second analysis unit 820 has a measuring unit for measuring an optical characteristic of a reaction solution after chemical reaction.

Figure 8:
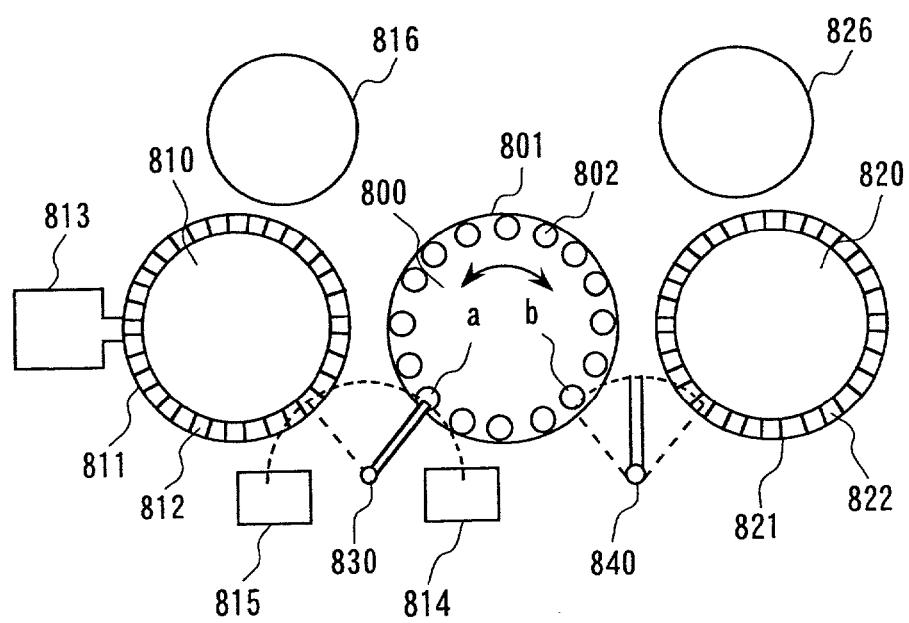
FIG. 8 is an outline of a configuration of an another embodiment in accordance with the present invention.

In the automatic analysis apparatus of FIG. 8, it is assumed that a specified sample requiring to be analyzed on both of an immune analysis item and a biochemical analysis item is contained in one specified sample bottle 802. When analysis is started for such a specified sample, the corresponding specified sample bottle is positioned at a sample sampling position by the sample disk 801. Then, the first pipetting device 830 coupled with the unused nozzle tip sucks a part of the specified sample into the nozzle tip and discharges it into the reaction container 812 on the reaction disk 811. An immune reaction between the sample and the reagent is progressed in the reaction container, and then an immune analysis item to be analyzed is measured.

The automatic analysis apparatus is programmed so that after finishing sample sampling to the above-mentioned specified sample bottle using the first pipetting device, the same sample bottle is positioned at a sample sampling Position b, and sample sampling using the second pipetting device 840 is performed. The specified sample pipetted to the reaction container 822 on the reaction disk 821 by the pipette nozzle of the second pipetting device is chemically reacted with the reagent in the reaction container, and the biochemical analysis item is measured based on photometrical measurement of the produced reaction solution.

Both of a biochemical analysis item and an immune analysis item can be also measured by the embodiment of FIG. 8, and the analysis measured value of the immune analysis item is not affected by the effect of carry-over between samples.

In a case of measuring a biochemical analysis item and an immune analysis item, the pipetting device using the disposable nozzle tip and the pipetting device using the repetitively used pipette nozzle are applied to a single sample bottle, and pipetting operation by the disposable nozzle tip is performed in prior to using the pipette nozzle. By doing so, the carry-over between samples caused by the pipette nozzle is avoided relating to the analysis item which should be extremely avoided, and the pipette nozzle used commonly can be used for sampling the sample relating to the biochemical analysis item.

Furthermore, the functions as shown in FIGS. 5 to 7 are performed in the embodiment shown in FIG. 8. In this case, the sampling processing effect becomes lower than that of the embodiment shown in FIG. 1. The control part controls respective mechanism of the analysis apparatus. In the analysis apparatus shown in FIG. 8, when the re-measurement is directed to be executed according to the measurement effect of the sample by the immune analysis unit 810, it is controlled that the sampling of the same sample is not performed by the second pipetting device 840 at the sampling position b until the first measurement result is obtained relating to the specified sample at the position a.

When the re-measurement is judged to need to be done, the corresponding specified sample is returned to the sampling position a by the sample disk 801, is sampled again by the first pipetting device 830, and is analyzed again by the immune analysis unit 810.

After this second time sampling, the corresponding sample is moved to the sampling position b, and is sampled by the second pipetting device 840.

Figure 9:
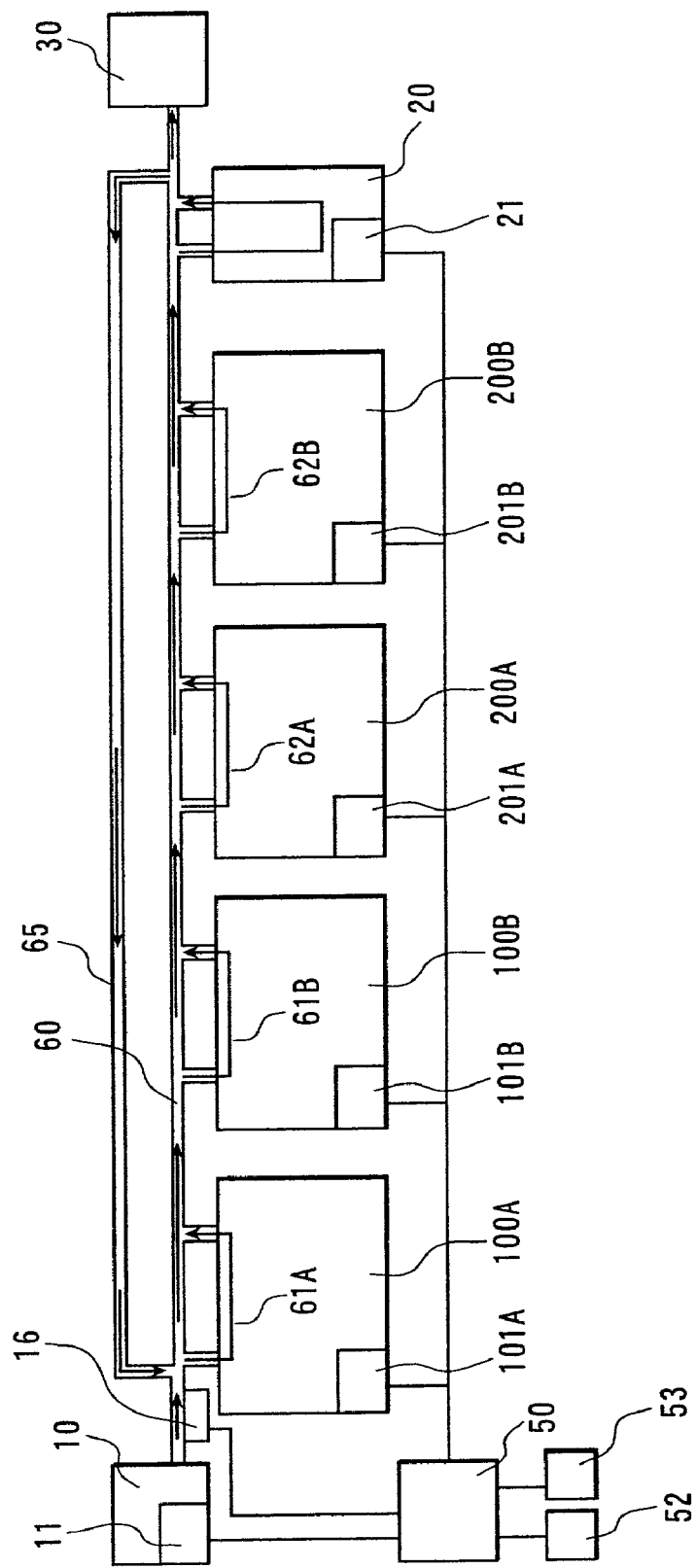
FIG. 9 is an outline of a configuration of the third embodiment in accordance with the present invention.

FIG. 9 shows an outline of a configuration of the third embodiment based on the present invention. The same functions of the elements in this embodiment as that in the former embodiment are shown by attaching the same reference numerals.

In FIG. 9, the analysis units 100A, 100B for measuring the immune analysis item and the analysis units 200A, 200B for measuring the biochemical analysis item are arranged along the rack transportation line 60. These analysis units are connected to be able to be disconnected to the rack transportation line 60.

The sample rack 2 supplied from the rack supply unit 10 can selectively drop in at the necessary analysis unit through the bypass lines 61A, 61B, 62A, 62B attached on the respective analysis units. The respective analysis units build in respective computers 101A, 101B, 201A, 201B as the analysis unit control parts.

The computer 11 built in the rack supply unit 10 performs necessary control of the rack supply unit 10, the rack transportation line 60, the returning line 65, and the rack stoker 30. The computer 21 built in the standby unit 20 performs necessary control in the standby unit 20. These computer and the bar code reader 16 are connected to computer 50 as the integrated controller. The computer 50 gives the necessary information to the computer 11 and the computer of the analysis unit which is planed to be dropped in by reading out the sample ID and the rack ID.

When the sample held by the sample rack is a sample which is specified to perform automatic re-examination and has an immune analysis item specified to perform automatic reexamination, after finishing the sampling for immune analysis, the sample rack is transported to the standby unit 20 by the transportation line 3 to be temporarily let stand by. During that period, the computer 50 judges based on a preset algorithm or logic whether or not re-examination is necessary. If the judged result is that the re-examination is necessary, the sample rack is returned to the entrance side of the rack transportation line 60 by the returning line 65. The sample rack is further transported to the suitable analysis unit by the rack transportation line 60, and the sample held by the sample rack is re-sampled and re-examined, that is, the immune analysis is performed on the sample again. After finishing sampling of the sample for the re-examination of immune analysis in the analysis unit, the sample rack is transported to the biochemical analysis unit and the sample is sampled to perform biochemical analysis. Then, the sample rack is transported to the rack stoker 30 by the rack transportation line 60 to be collected there without dropping in at the other analysis unit nor the standby unit 20 when the sample held by the sample rack is not specified to perform re-examination.

The analysis units 100A, 100B have the same construction with that of the analysis unit 100 shown in FIG. 1, and the analysis units 200A, 200B have the same construction with that of the analysis unit 200 shown in FIG. 1.

Figure 10:
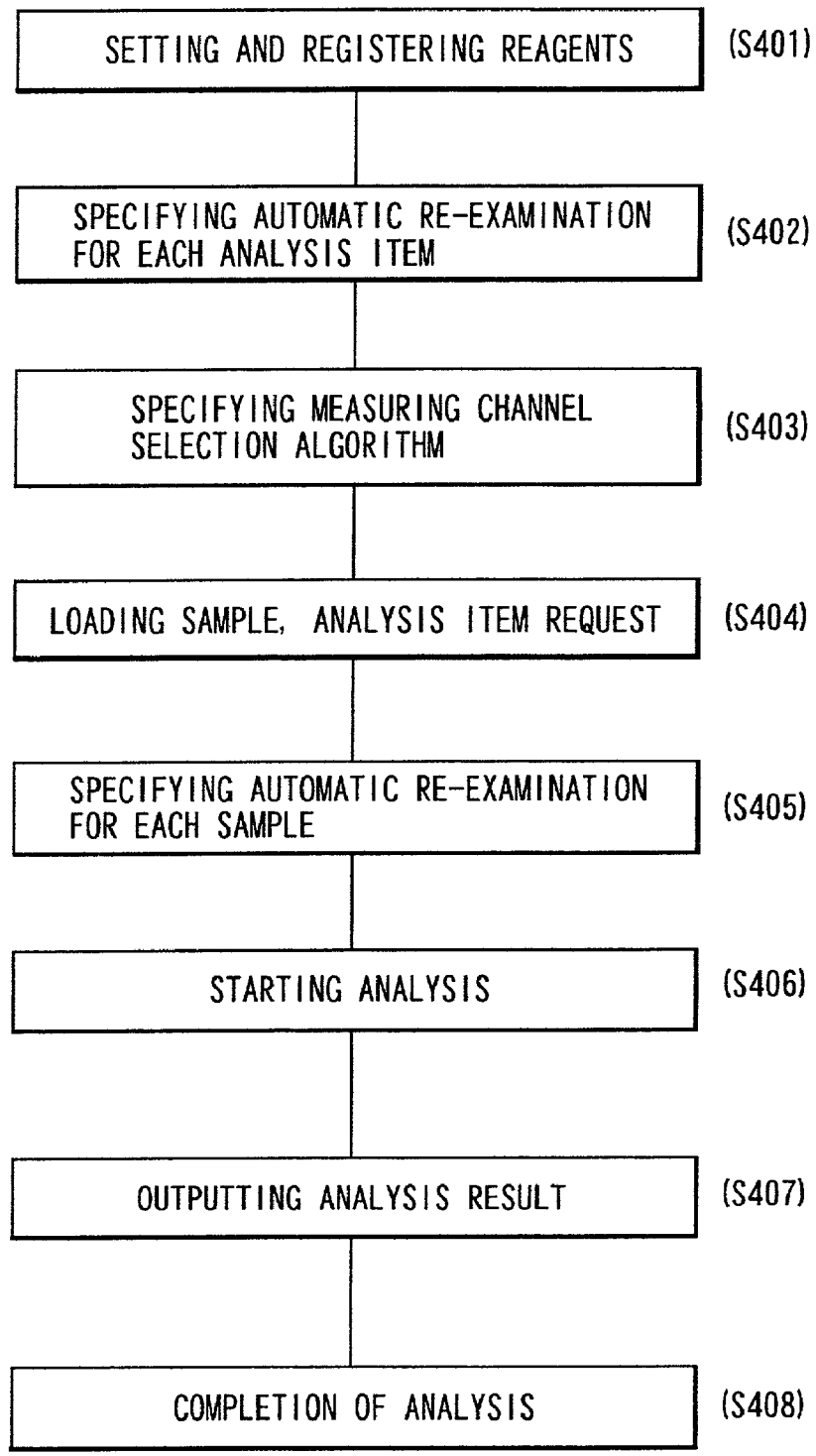
FIG. 10 is a view for explaining an operating flow of the analysis apparatus shown in FIG. 9.

FIG. 10 is a flow chart of the system operation of an automatic analysis apparatus in accordance with the present invention. An operator initially sets reagents at preset positions in each analysis unit, and information which analysis unit each reagent exists in and which analysis item each reagent is to be used for is stored and registered in a memory unit in the computer 50 (S401). The registration may be performed by operating the operating unit 18 by the operator, or by automatically reading a-reagent ID having each of the reagent bottles 217, 218.

Next, the operator operates the operating unit 52 to specify whether or not the automatic re-examination logic function is put in action and which re-examination logic is put in action if re-examination logic is put in action (S402). This is for automatically performing re-examination only on an analysis item which really requires re-examination, and largely contributes to suppress decrease in processing capacity of the whole apparatus. In detail, the automatic re-examination logic is a logic showing, for example, the following conditions. The conditions are pre-stored and pre-registered in the memory unit 51 of the computer 50, and the operator can select one by designating any one condition, and the designation of the re-examination of the corresponding analysis item can be cancelled. The automatic re-examination logic is selected through the screen of the CRT 53.

(1) The automatic re-measurement is always performed without any condition.
(2) The automatic re-measurement is performed when an analysis result departs from an analysis (measurement) range preset for each analysis item. For example, in regard to TSH (thyrotropin : thyroid-stimulating hormone), when a first analysis result is above 0.27 IU/ml, but departs from a condition below 4.2 IU/ml, the re-measurement is performed.
(3) The automatic re-measurement is performed when a difference between an analysis value in this time and an analysis value in the preceding time(or an analysis value before the preceding time) on samples from a single person exceeds a preset limit value (for example, when the analysis value in this time differs from the analysis value in the preceding time by 50% or more).

After that, the operator operates the operating unit 52 to specify an analysis (measurement) channel using algorithm when the re-examination is performed relating to the analysis item (S403). In detail, the analysis channel using algorithm is a algorithm showing, for example, the following conditions. The conditions are pre-stored and pre-registered in the memory part 51 of the computer 50, and the operator can be specify and select one condition. The one analysis channel means a combination of one reaction line and one sensor.

(1) The same analysis (measurement) channel as an analysis channel used for the analysis (measurement) in the time before the re-examination is used.
(2) An analysis channel different from an analysis channel used for the analysis in the time before the re-examination is used. This condition is effective when the analysis channel used in the time before the re-examination is abnormal.
(3) A plurality of analysis channels including the same analysis channel used for the analysis in the time before the re-examination are used. This condition is effective when a highly reliable analysis result is attempted to be obtained.
(4) A plurality of analysis channels excluding the same analysis channel used for the analysis in the time before the re-examination are used. This condition is effective when the analysis channel used in the time before the re-examination is abnormal and a highly reliable analysis result is attempted to be obtained.

Although each of the analysis units in the FIG. 1 and FIG. 9 has only one analysis (measuring) channel, each of the analysis units may have a plurality of analysis channels. The plurality of analysis channels in the above items (3) and (4) may have a plurality of analysis channels in one analysis unit, or may have a plurality of analysis channels extending over a plurality of analysis units within a same immune analysis.

The automatic re-examination logic information and the analysis channel using algorithm may be stored and registered not in the memory part 51 in the computer 50 but in a memory unit 55 provided in the external.

Then, after the registration, the operator loading the sample rack to the sample rack loading unit 1, and operates the operating unit 52 to register to the computer 50 which sample is analyzed on which analysis item, that is, register analysis item request (S404). Successively, the operator operates the operating unit 52 to specify for each sample whether or not the automatic re-examination logic described above is executed by using the screen of the CRT 53 (S405). This is effective for a small amount of an important sample in that the unnecessary consumption of the important sample can be prevented by omitting the automatic re-examination. After finishing the abovementioned operations by the operator, analysis operation is started (S406), and a result of the analysis is output (S407), and thus the analysis is completed (S408).

Figure 11A:
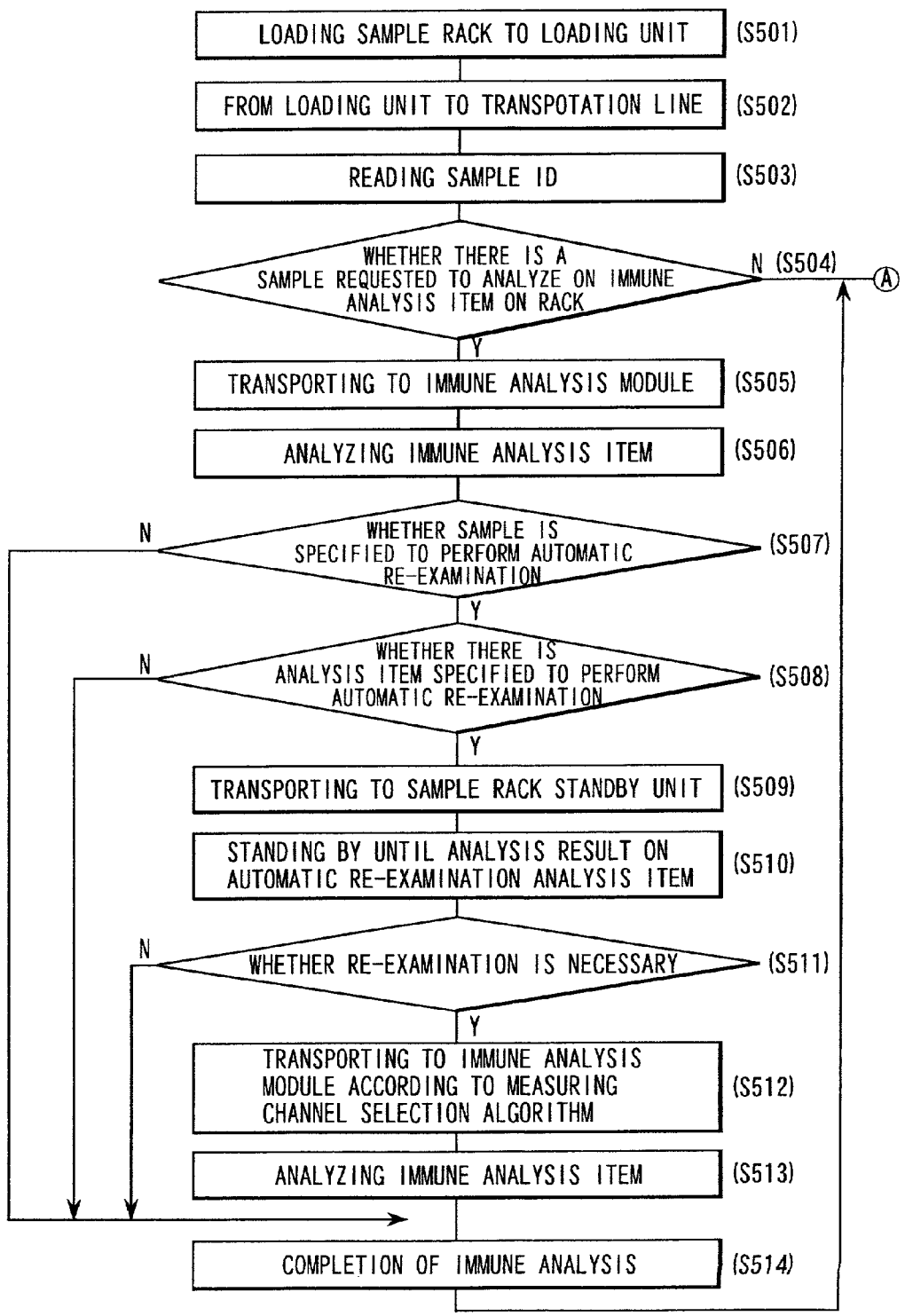
FIGS. 11A and 11B respectively are views for showing a process flow for transporting the sample rack of the analysis apparatus shown in FIG. 9.
Figure 11B:
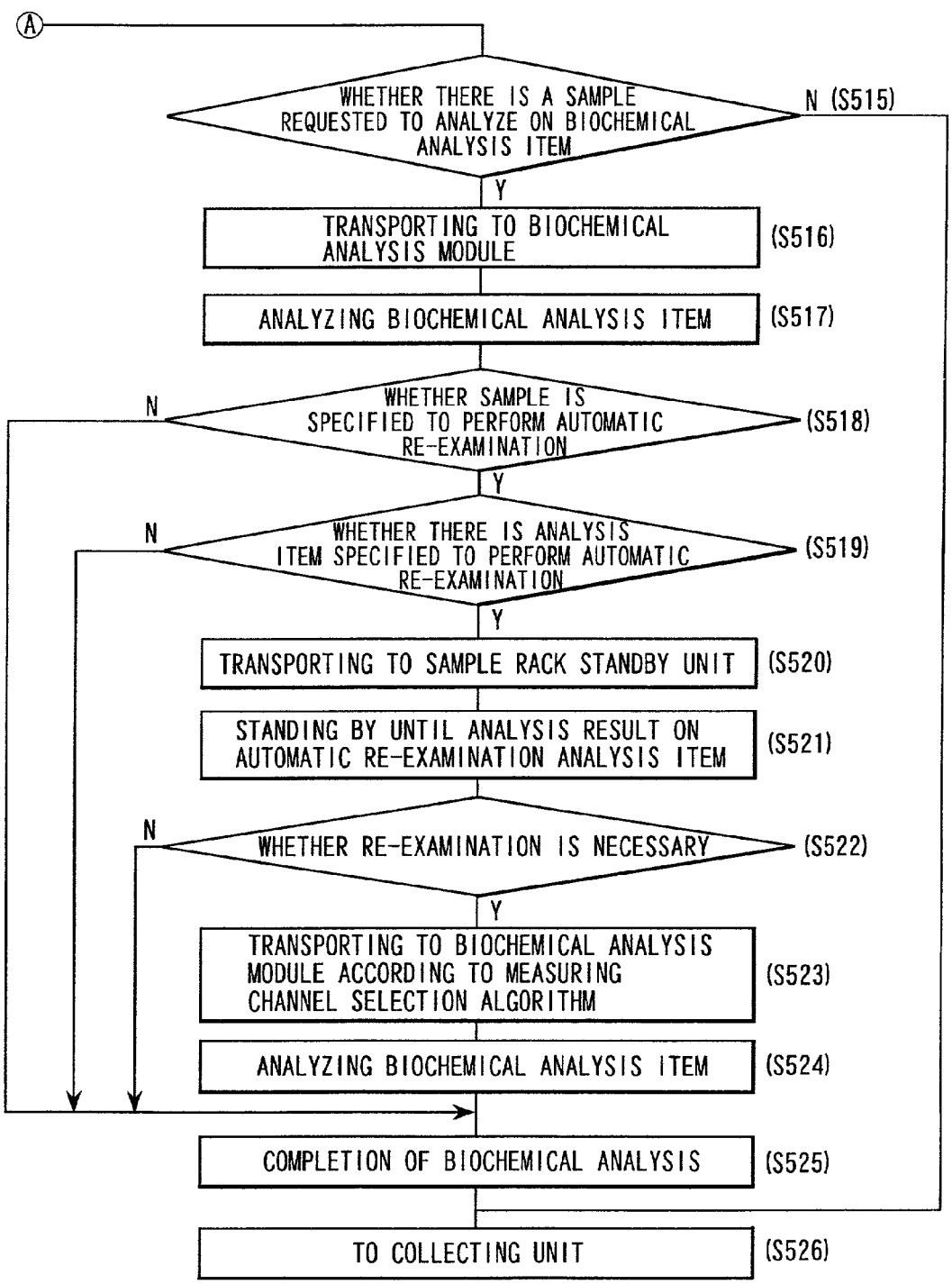

FIGS. 11A and 11B are flow-charts of sample rack transportation processing in accordance with the present invention. A sample rack is loaded in the rack supply unit 10 (S501). When the loaded sample rack is transported to the rack transportation line 60 (S502), the sample ID and the rack ID are read by the ID reading unit 16 (S503) and the information is transmitted to the computer 50.

The computer 50 judges whether or not there is a sample requested to analyze on an immune analysis item on the rack (S504). If the result is "YES", the sample rack is transported to a specified immune analysis unit by the rack transportation line 60 based on a command from the computer 50 to the computer 11 (S505). The sample sampling is performed based on a command from the computer 50 to the computer of the immune analysis unit, and immune analysis is performed on the immune analysis item (S506).

After finishing the sampling, the computer 50 judges whether or not the sampled sample is a sample specified automatic re-examination in Step S405 of FIG. 10 (S507). If the result is "YES", the computer 11 judges whether or not the immune analysis item specified in Step S405 of FIG. 10 to perform automatic re-examination is included in the sample (S508). If the result is "YES", the rack is transported to the sample rack standby unit 9 by the rack transportation line 60 based on a command from the computer 50 to the computer 11 (S509) and the rack stands by there until the analysis result is output (S510).

After outputting the result of the above analysis, the computer 50 judges based on the re-examination logic specified in Step S402 of FIG. 10 whether or not re-examination is necessary (S511). If the result is "YES", the sample rack is transported to an specified immune analysis unit by the returning line 65 and the rack transportation line 60 according to the selected analysis channel using algorithm based on a command from the computer 50 to the computer 11 (S512). Pipetting is performed based on a command from the computer 50 to the computer of the analysis unit (S513), and thus, the immune analysis is completed (S514).

If the judged result in Step S507, S508 or S511 is "NO", the flow proceeds to Step S514.

After finishing Step S514 or if the judged result in Step S504 is "NO", Steps S515 to S525 of biochemical analysis corresponding to Steps S504 to S514 of immune analysis are similarly performed, respectively. After finishing the analysis or when the analysis is necessary, the sample rack is collected to the rack stoker 30 (S526).

FIG. 12 shows an example of a partial arrangement of another embodiment of an automatic analysis apparatus in accordance with the present invention. This embodiment is different from the embodiment of FIGS. 1 and 9 in the point that each analysis unit does not have any siding(by-pass line) as shown in FIGS. 1 and 9. Therefore, in this embodiment, the sample rack is kept on the rack transportation line 60 even during sample sampling.

In the analysis apparatus shown in FIG. 12, at respective lower flow side of the analysis units 100a, 100B, 200A, 200B, the standby units 20A, 20B, 20C, 20D are arranged corresponding to the respective analysis units. The movement of the sample rack transmitted to the standby units is little different from that of the example shown in FIG. 1 or 9.

For example, in a case that the re-measurement by the same analysis unit is needed relating to the sample rack in the standby unit 20B attached to the analysis unit 100B, the sample rack is moved from the standby unit 20B to the returning line 65, and is moved to the rack transportation line 60 near the entrance of the standby unit 20A, and again stops at the sample sampling position of the analysis unit 100B (upper the transportation line 60) so as to be sampled.

If the sample on the sample rack in the standby unit 20B does not need to be re-measured, the sample rack is moved from the standby unit 20B to the rack transportation line 60, and is transferred to the sample sampling position of the biochemical analysis unit 200A, for example. In this case, the sample rack does not passes by the returning line 65.

What is claimed is:

1. A method of analyzing a body liquid using an analysis apparatus comprising a plurality of analysis units, each having a pipette nozzle to perform a sample sampling function; and at least one sample to be analyzed by the plurality of analysis units; and wherein said apparatus is capable of performing sample sampling relating to an analysis item suitable for each of said plurality of analysis units, wherein said plurality of analysis units includes a first analysis unit for receiving said at least one sample sampled by a respective pipette nozzle including a detachable nozzle tip; wherein said respective detachable nozzle tip is exchanged when said at least one sample is changed; and a second analysis unit for receiving said at least one sample sampled by a respective pipette nozzle; wherein said pipette nozzle of said second analysis unit is used commonly to sample said at least one sample and other different samples that may be therein; the method comprising:

(a) selecting a specified sample to be analyzed on a plurality of analysis items having different avoiding levels of carry-over, wherein an analysis item of said first analysis unit has a higher avoiding level of carry-over than an analysis item of said second analysis unit;

(b) executing sample sampling of said specified sample relating to said analysis item having a higher avoiding level of carry-over for said first analysis unit; (c) judging if the carry-over level analyzed in said first analysis unit needs to be re-measured; and (d) after said analysis item having said higher avoiding level of carry-over analyzed in said first analysis unit is judged not to need re-measurement, executing sample sampling of said specified sample relating to said analysis item having a lower avoiding level of carry-over for said second analysis unit.

* * * * *